US005667987A

United States Patent [19]
Buckbinder et al.

[11] Patent Number: 5,667,987
[45] Date of Patent: Sep. 16, 1997

[54] P53 RESPONSE GENES

[75] Inventors: Leonard Buckbinder, Doylestown, Pa.; Randy Talbott, Freehold, N.J.; Bernd R. Seizinger, Stockton, N.J.; Nikolai Kley, Princeton Junction, N.J.

[73] Assignee: Bristol-Myers Squibb Company, New York, N.Y.

[21] Appl. No.: 274,318

[22] Filed: Jul. 12, 1994

[51] Int. Cl.$^6$ .......................... C12P 21/02; C12N 15/63; C12N 1/21; C07H 21/04
[52] U.S. Cl. ................ 435/69.1; 435/320.1; 435/252.3; 435/254.11; 536/23.5
[58] Field of Search ............................ 435/69.1, 320.1, 435/252.3, 254.11; 536/23.5

[56] References Cited

PUBLICATIONS

Levine, A.J. et al., "The p53 tumour suppressor gene" (1991) Nature, 351,453–455.

Vogelstein, B. and Kinzler, K.W., "p53 function and dysfunction" (1992) Cell, 70, 523–526.

Zambetti, G. and Levine, A.J., "A comparison of the biological activities of wild–type and mutant p53" (1993) FASEB J., 7, 855–865.

Harris, C.C., "p53: At the crossroads of molecular carcinogensis and risk assessment" (1993) Science, 262, 1980–1981.

Lane, D.P., "p53, guardian of the genome" (1992)Nature, 358, 15–16.

Livingstone, L.R. et al., "Altered cell cycle arrest and gene amplification potential accompany loss of wild–type p53" (1992) Cell, 70, 923–935.

Chen, P.–L. et al., "Genetic mechanisms of tumor suppression by the human p53 genome" (1990) Science, 250, 1576–1580.

Dittmer, D. et al., "Gain of function mutations in p53" (1993) Nature Genetics, 4, 4142–4145.

Sun, Y. et al., "Progression toward minor cell phenotype is enhanced by overexpression of a mutant p53 tumor–suppressor gene isolated from nasopharyngeal carcinoma" (1993) Proc. Natl. Acad. Sci. USA, 90, 2827–2831.

Ginsberg, D. et al., "Wild–type p53 can down–modulate the activity of various promoters" (1991) Proc. Natl. Acad. Sci. USA, 88, 9979–9983.

Santhanam, U. et al., "Repression of the interleukin 6 gene promoter by p53 and the retinoblastoma susceptibility gene product" (1991) Proc. Natl. Acad. Sci. USA, 88, 7605–7609.

Kley, N. et al., "Repression of the basal c–fos promoter by wild–type p53" (1992) Nucleic Acids Res., 20, 4083–4087.

Mack, D.H. et al., "Specific repression of TATA–mediated but not initiator–mediated transcription by wild–type p53" (1993) Nature, 363, 281–283.

Seto, E. et al., "Wild–type p53 binds to the TATA–binding protein and represses transcription" (1992) Proc. Natl Acad. Sci. USA, 89, 12028–12032.

Truant, R. et al., "Direct interaction between the transcriptional activation domain of human p53 and the TATA box–binding protein" (1993) J. Biol. Chem., 268, 2284–2287.

Liu, X. et al., "The p53 activation domain binds the TATA box–binding polypeptide in holo–TFHD, and a neighboring p53 domain inhibits transcription" (1993) Mol. Cell. Biol., 13, 3291–3300.

El–Diery, W.S. et al., "Definition of a consensus binding site for p53" (1992) Nature Genetics 1, 45–49.

Funk, W.D. et al., "A transcriptionally active DNA–binding site for human p53 protein complexes" (1992) Mol. Cell. Biol., 12, 2866–2871.

Weintraub, H. et al., "The MCK enhancer contains a p53 responsive element" (1991) Proc. Natl. Acad. Sci. USA, 88, 4570–4571.

Kern, S.E. et al., "Oncogenic forms of p53 inhibit p53–regulated gene expression" (1992) Science, 256, 827–830.

Farmer, G. et al., "Wild–type p53 activates transcription in vitro" (1992) Nature, 358, 83–86.

Zambetti, G.P. et al., "Wild–type p53 mediates positive regulation of gene expression through a specific DNA sequence element" (1992) Genes & Development, 6, 1143–1152.

Yonish–Rouach, E. et al., "Wild–type p53 induces apoptosis of myeloid leukaemic cells that is inhibited by interleukin–6" (1991) Nature, 352, 345–347.

Lowe, S.W. et al., "p53 is required for radiation–induced apoptosis in mouse thymocytes" (1993) Nature, 362, 847–849.

Clarke, A.R. et al., "Thymocyte apoptosis induced by p53–dependent and independent pathways" (1993) Nature, 362, 849–852.

Shaw, P. et al., "Induction of apoptosis by wild–type p53 in a human colon tumor–derived cell line" (1992) Proc. Natl. Acad. Sci. USA, 89, 4495–4499.

Wu, X. et al., "The p53–mdm–2 autoregulatory feedback loop" (1993) Genes & Development, 7, 1126–1132.

Kastan, M.B. et al., "A mammalian cell cycle checkpoint pathway utilizing p53 and GADD45 is defective in ataxia–telangiectasia" (1992) Cell, 71, 587–597.

El–Diery, W.S. et al., "WAF1, a potential mediator of p53 tumor suppression" (1993) Cell, 75, 817–825.

Oliner, J.D. et al., "Amplification of a gene encoding a p53–associated protein in human sarcomas" (1992) Nature, 358, 80–83.

(List continued on next page.)

*Primary Examiner*—Robert A. Wax
*Assistant Examiner*—Kawai Lau
*Attorney, Agent, or Firm*—James M. Bogden

[57] ABSTRACT

Nucleic acid sequences, particularly DNA sequences, coding for all or part of p53 response protein PIGI-1, expression vectors containing the DNA sequences, host cells containing the expression vectors, and methods utilizing these materials are disclosed. The invention also concerns polypeptide molecules comprising all or part of p53 response protein PIGI-1, and methods for producing these polypeptide molecules.

22 Claims, 13 Drawing Sheets

PUBLICATIONS

Harper, J.W. et al., "The p21 Cdk-interacting protein Cip1 is a potential inhibitor of G1 cyclin-dependent kinases" (1993) Cell, 75, 805–816.

Xiong, Y. et al., "p21 is a universal inhibitor of cyclin kinases" (1993) Nature, 366, 701–704.

Wang, Z. and Brown, D.D., "A gene expression screen" (1991) Proc. Natl. Acad. Sci. USA, 88, 11505–11509.

Gossen, M. and Bujard, H., "Tight control of gene expression in mammalian cells by tetracycline-responsive promoters" (1992) Proc. Natl. Acad. Sci. USA, 89, 5547–5551.

Baker, S.J. et al., "Suppression of human colorectal carcinoma cell growth by wild-type p53" (1990) Science, 249, 912–915.

Unger, T. et al. "p53: A transdominant regulator of transcription whose function is ablated by mutations occurring in human cancer" (1992) EMBO J., 11, 1383–1390.

Kern, S.E. et al., "Identification of p53 as a sequence-specific DNA-binding protein" (1991) Science, 252, 1708–1711.

Buckbinder, L. and Brown, D.D., "Thyroid hormone-induced gene expression changes in the developing frog limb" (1992) J. Biol. Chem., 267, 25786–25791.

El-Diery, W.S. et al., "WAF1/CIP1 is induced in p53-mediated $G_1$ arrest and apoptosis" (1994) Cancer Res., 54, 1169–1174.

```
   1  GGGGCTACCG CGCCTTTGCT TCCTGGCGCA CGCGGAGCCT CCTGGAGCCT
  51  GCCACCATCC TGCCTACTAC GTGCTGCCCT GCGCCCGCAG CCATGTGCCG
 101  CACCCTGGCC GCCTTCCCCA CCACCTGCCT GGAGAGAGCC AAAGAGTTCA
 151  AGACACGTCT GGGGATCTTT CTTCACAAAT CAGAGCTGGG CTGCGATACT
 201  GGGAGTACTG GCAAGTCCGA GTGGGCAGT AAACACAGCA AAGAGAATAG
 251  AAACTTCTCA GAAGATGTGC TGGGGTGGAG AGAGTCGTTC GACCTGCTGC
 301  TGAGCAGTAA AAATGGAGTG GCTGCCTTCC ACGCTTTCCT GAAGACAGAG
 351  TTCAGTGAGG AGAACCTGGA GTTCTGGCTG GCCTGTGAGG AGTTCAAGAA
 401  GATCCGATCA GCTACCAAGC TGGCCTCCAG GGCACACCAG ATCTTTGAGG
 451  AGTTCATTTG CAGTGAGGCC CCTAAAGAGG TCAACATTGA CCATGAGACC
 501  CGCGAGCTGA CGAGGATGAA CCTGCAGACT GCCACAGCCA CATGCTTTGA
 551  TGCGGCTCAG GGGAAGACAC GTACCCTGAT GGAGAAGGAC TCCTACCCAC
 601  GCTTCCTGAA GTCGCCTGCT TACCGGGACC TGGCTGCCCA AGCCTCAGCC
 651  GCCTCTGCCA CTCTGTCCAG CTGCAGCCTG ACGAGCCCT CACACACCTG
 701  AGTCTCCACG GCAGTGAGGA AGCCAGCCGG GAAGAGAGGT TGAGTCACCC
 751  ATCCCCGAGG TGGCTGCCCC TGTGTGGGAG GCAGGTTCTG CAAAGCAAGT
 801  GCAAGAGGAC AAAAAAAAAA AAAAAAAAA AAAAAATGCG CTCCAGCAGC
 851  CTGTTTGGGA AGCAGCAGTC TCTCCTTCAG ATACTGTGGG ACTCATGCTG
 901  GAGAGGAGCC GCCCACTTCC AGGACCTGTG AATAAGGGCT AATGATGAGG
 951  GTTGGTGGGG CTCTCTGTGG GGCAAAAAGG TGGTATGGGG GTTAGCACTG
1001  GCTCTCGTTC TCACCGGAGA AGGAAGTGTT CTAGTGTGGT TTAGGAAACA
1051  TGTGGATAAA GGGAACCATG AAAATGAGAG GAGGAAAGAC ATCCAGATCA
1101  GCTGTTTTGC CTGTTGCTCA GTTGACTCTG ATTGCATCCT GTTTTCCTAA
1151  TTCCCAGACT GTTCTGGGCA CGGAAGGGAC CCTGGATGTG GAGTCTTCCC
1201  CTTTGGCCCT CCTCACTGGC CTCTGGGCTA GCCCAGAGTC CCTTAGCTTG
1251  TACCTCGTAA CACTCCTGTG TGTCTGTCCA GCCTTGCAGT CATGTCAAGG
1301  CCAGCAAGCT GATGTGACTC TTGCCCCATG CGAGATATTT ATACCTCAAA
1351  CACTGGCCTG TGAGCCCTTT CCAAGTCAGT GGAGAGCCCT GAAAGGAGGC
```

Figure 6-1

```
1401 TCACTTGAAT CCAGCTCAGT GCTCTGGGTG GCCCCCTGCA GGTGGCCCCT

1451 GACCCTGCGT TGCAGCAGGG TCCACCTGTG AGCAGGCCCG CCCTGGGGCC

1501 TCTTCCTGGA TGTGCCCTCT CTGAGTTCTG TGCTGTCTCT TGGAGGCAGG

1551 GCCCAGGAGA ACAAAGTGTG GAGGCCTCGG GGAGTGGCTT TTCCAGCTCT

1601 CATGCCCCGC AGTGTGGAAC AAGGCAGAAA AGGATCCTAG GAAATAAGTC

1651 TCTTGGCGGT CCCTGAGAGT CCTGCTGAAA TCCAGCCAGT GTTTTTTGTG

1701 GTATGAGAAC AGGCAAAAAG AGATGCCCCG AGATAGAAGG GGAGCCTTGT

1751 GTTTCTTTCC TGCAGACGTG AGATGAACAC TGGAGTGGGC AGAGGTGGCC

1801 CAGGACCATG GCACCCTTAG AGTGCAGAAG CTGGGGGGAG AGGCTGCTTC

1851 GAAGGGCAGG ACTGGGGATA CCTGCCTGTC ACCTCAGGGC ATCACTGAAC

1901 AAACATTTCC TGATGGGAAC TCCTGCGGCA GAGCCCAGGC TGGGGAAGTG

1951 AACTACCCAG GGCAGCCCCT TTGTGGCCCA GGATAATCAA CACTGTTCTC

2001 TCTGTACCAT GAGCTCCTCC AGGAGATTAT TTAAGTGTAT TGTATCATTG

2051 GTTTTCTGTG ATTGTCATAA CATTGTTTTT GTTATTGTTG GTGCTGTTGT

2101 TATTTATTAT TGTAATTTCA GTTGCCTCT ACTGGAGAAT CTCAGCAGGG

2151 GTTTCAGCCT GACTGTCTCC CTTTCTCTAC CAGACTCTAC CTCTGAATGT

2201 GCTGGGAACC TCTTGGAGCC TGTCAGGAAC TCCTCACTGT TTAAATATTT

2251 ATTTATTGTG ACAAATGGAG CTGGTTTCCT AGATATGAAT GATGTTTGCA

2301 ATCCCCATTT TCCTGTTTCA GCATGTTATA TTCTTATAAA ATAAAAGCAA

2351 AAGTCAAATA TGAAAAAAAA AAAAAAAAA AAA
```

Figure 6-2

```
  1  MCRTLAAFPT TCLERAKEFK TRLGIFLHKS ELGCDTGSTG KSEWGSKHSK

51  ENRNFSEDVL GWRESFDLLL SSKNGVAAFH AFLKTEFSEE NLEFWLACEE

101  FKKIRSATKL ASRAHQIFEE FICSEAPKEV NIDHETRELT RMNLQTATAT

151  CFDAAQGKTR TLMEKDSYPR FLKSPAYRDL AAQASAASAT LSSCSLDEPS

| NAME | POSITION |
|---|---|
| LB-36 | 1198-1178 |
| LB-37 | 851-870 |
| LB-38 | 1166-1146 |
| LB-39 | 1146-1166 |
| LB-44 | 871-851 |
| LB-49 | 492-472 |
| LB-50 | 528-508 |
| LB-52 | 1458-1466 |
| LB-56 | 654-673 |
| LB-57 | 1042-1023 |
| LB-58 | 1023-1042 |
| LB-59 | 1572-1553 |
| LB-60 | 1613-1632 |
| LB-61 | 1813-1832 |
| LB-62 | 2146-2127 |
| LB-63 | 2127-2146 |
| LB-64 | 1937-1917 |
| LB-67 | 434-454 |
| RT-77 | 455-434 |
| RT-83 | 302-286 |
| RT-84 | 234-253 |
| RT-85 | 15-34 |
| RT-86 | 144-125 |

P53 RESPONSE GENES

FIELD OF THE INVENTION

This invention relates to novel p53 response genes, expression vectors comprising the genes, host cells comprising the expression vectors, proteins produced by the genes, methods for producing the proteins, and methods of using the genes and proteins.

BACKGROUND OF THE INVENTION

Inactivation or loss of p53 is a common event associated with the development of human cancers. Functional inactivation may occur as a consequence of genetic aberrations within the p53 gene, most commonly missense mutations, or interaction with vital and cellular oncogenes [for reviews see: Levine, A. J. et al, Nature 351,453–455 (1991), Vogelstein, B. and Kinzler, K. W., Cell 70, 523–526 (1992), Zambetti, G., and Levine, A. J., FASEB J. 7, 855–865 (1993), Harris, C. C., Science 262, 1980–1981 (1993)]. Loss of wild-type (wt) p53 functions leads to uncontrolled cell cycling and replication, inefficient DNA repair, selective growth advantage and, consequently, tumor formation [Levine, A. J. et al, Nature 351, 453–455 (1991); Vogelstein, B. and Kinzler, K. W., Cell 70, 523–526 (1992); Zambetti G. and Levine, A. J., FASEB J. 7, 855–865 (1993); Harris, C. C., Science 262, 1980–1981, (1993); Lane, D. P., Nature 358, 15–16 (1992); Livingstone, L. R. et al, Cell 70, 923–935 (1992)]. Tumorigenesis may be even further accentuated by the gain of new functions associated with many mutant forms of p53 [Chen, P.-L. et al, Science 250, 1576–1580 (1990); Dittmer, D. et al, Nature Genetics 4, 4142–4145 (1993); Sun, Y. et al, Proc. Natl Acad. Sci. U.S.A. 90, 2827–283 1 (1993)], providing a potential basis for their strong selection in human tumors.

The mechanism(s) underlying p53 mediated growth suppression is still ill defined. However, of particular interest is the ability of p53 to act as a transcription factor, a function which strongly correlates with its ability to act as a tumor suppressor. p53 has been shown to suppress a variety of promoters containing TATA elements [e.g. Ginsberg, D. et al, Proc. Natl. Acad. Sci. U.S.A. 88, 9979–9983 (1993), Santhanam, U. et al, Proc. Natl. Acad. Sci. U.S.A. 88, 7605–7609 (1993), Kley, N. et al, Nucleic Acids Res. 20, 4083–4087 (1992), Mack, D. H. et al, Nature 363, 281–283 (1993)]. This suppression is sequence independent and may involve p53 binding to components of the basal transcription machinery, such as the TATA-binding protein [e.g. Sero, E. et al, Proc. Natl. Acad. Sci. U.S.A. 89, 12028–12032 (1992), Truant, R. et al, J. Biol. Chem. 268, 2284–2287 (1993), Liu, X. et al, Mol. Cell. Biol. 13, 3291–3300 (1993)]. In contrast, transactivation by p53 is sequence dependent and correlates with its binding to specific DNA sequences such as the recently reported consensus-binding site [El-Deiry, W. S. et al, Nature Genetics 1, 45–49 (1992), Funk, W. D. et al, Mol. Cell. Biol. 12, 2866–2871 (1992)]. p53 can efficiently activate transcription from promoters bearing such sites, both in vivo and in vitro [e.g. Kley, N. et al, Nucleic Acids Res. 20, 4083–4087 (1992), Seto, E. et al, Proc. Natl. Acad. Sci. U.S.A. 89, 12028–12032 (1992), Weintraub, H. et al, Proc. Natl. Acad. Sci. U.S.A. 88, 4570–4574 (1991), Kern, S. E. et al, Science 256, 827–830 (1992), Farmer, G. et al, Nature 358, 83–86 (1992), Zambetti, G. P. et al, Genes & Development 6, 1143–1152 (1992)]. Most oncogenic mutants of p53 have lost both the transcription suppression and sequence specific transactivation properties displayed by wild-type p53.

The strong correlation between the ability of p53 to activate transcription in a sequence specific manner and its ability to suppress cell growth or induce apoptosis [Vogelstein, B. and Kinzler, K. W., Cell 70, 523–526 (1992), Yonish-Rouach, E. et al, Nature 352, 345–347 (1991), Lowe, S. W. et al, Nature 362, 847–849 (1993), Clark, A. R. et al, Nature 362, 849–852 (1993), Shaw, P. et al, Proc. Natl. Acad. Sci. U.S.A. 89, 4495–4499 (1992)], suggests that p53-induced genes may play a critical role in mediating the function of p53 as a tumor suppressor. A few endogenous genes have been characterized to be induced by p53. These include the mdm-2 and its human homolog hdm-2 [Wu, X. et al, Genes & Development 7, 1126–1132 (1993)], GADD45 [Kastan, M. B. et al, Cell 71, 587–597 (1992)], and WAF1/CIP1/p21 [El-Deiry, W. S., et al, Cell 75, 817–825 (1993)] genes. hdm-2 has been suggested to act as a negative feedback regulator of p53, and in this respect would function as an oncogene [Wu, X. et al, Genes & Development 7, 1126–1132 (1993), Zambetti, G. and Levine, A. J., FASEB J. 7, 855–865 (1993)]. This is consistent with amplification of the hdm-2 gene being associated with human cancers [Oliner, J. D. et al, Nature 358, 80–83 (1992)]. Both WAF1/CIP1/p21, an inhibitor of cyclin-dependent kinases [Harper, J. W. et al, Cell 75, 805–816 (1993), Xiong, Y. et al, Nature 366, 701–704 (1993)], and gadd45 [Zhan, Q. et al, Mol. Cell. Biol. 14, 2361–2371 (1994)] have so far been shown to inhibit growth of tumor cells in culture [El-Deiry, W. S. et al, Cell 75, 817–825 (1993)].

SUMMARY OF THE INVENTION

The present invention involves the isolation of a p53 upregulated gene.

In particular, the present invention concerns an isolated nucleic acid molecule comprising a nucleic acid sequence coding for all or part of p53 response protein having the amino acid sequence shown in FIG. 7 [SEQ ID NO: 2]. This protein is sometimes referred to hereinafter as "p53 response protein PIGI-1" (p53 induced growth inhibitor 1) or "PIGI-1 protein." Preferably, the nucleic acid molecule is a DNA (deoxyribonucleic acid) molecule, and the nucleic acid sequence is a DNA sequence. Further preferred is a DNA sequence having all or part of the nucleotide sequence as shown in FIG. 6 [SEQ ID NO: 1].

The present invention also concerns a nucleic acid molecule having a sequence complementary to the above nucleic acid sequences coding for all or part of the p53 response protein having the amino acid sequence shown in FIG. 7 [SEQ ID NO: 2].

The present invention further concerns expression vectors comprising a DNA sequence coding for all or part of the p53 response protein having the amino acid sequence shown in FIG. 7 [SEQ ID NO: 2].

The present invention additionally concerns prokaryotic or eukaryotic host cells containing an expression vector that comprises a DNA sequence coding for all or part of the p53 response protein having the amino acid sequence shown in FIG. 7 [SEQ ID NO: 2].

The present invention additionally concerns polypeptides molecules comprising all or part of the novel p53 response protein having the amino acid sequence shown in FIG. 7 [SEQ ID NO: 2].

The present invention also concerns methods for detecting nucleic acid sequences coding for all or part of the novel p53 response protein having the amino acid sequence shown in FIG. 7 [SEQ ID NO: 2] or related nucleic acid sequences.

Parental EB and clonal EB 1 cells (containing wild-type p53 under control of the metallothionein promoter), were treated with vehicle (water) or CdCl$_2$ (6 uM) for 10 hours as indicated. Poly-adenylated RNA was isolated and Northern blots were prepared in quadruplicate. Blots were hybridized with probes for clones A28, A26, W4.5 or β-actin. Autoradiograms are shown with the position of molecular weight markers indicated on the left.

FIG. 6. Nucleotide sequence of the cDNA encoding p53 response protein PIGI-1.

FIG. 7. Predicted amino acid sequence of the p53 response protein PIGI-1.

Figure 8:
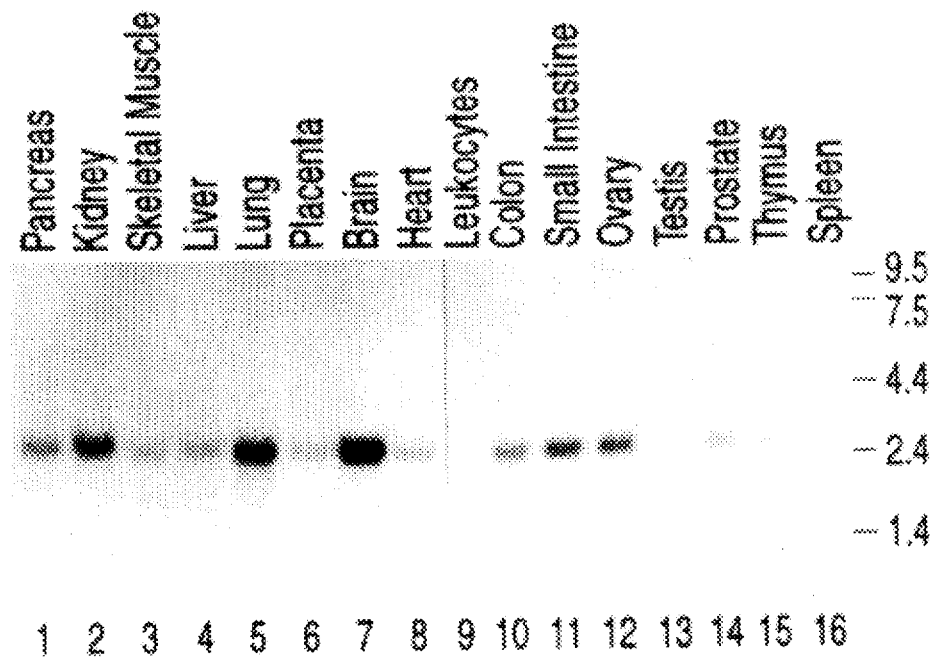

FIG. 8. Northern blot analysis of p53 response protein PIGI-1 expression in different human tissues.

2.5 ug of poly-adenylated RNA from the indicated adult human tissues was used to prepare Northern blots (Clonetech, Palo Alto, Calif.). The blots were hybridized with a $^{32}$P labeled cDNA probe corresponding to cDNA fragment A28 and visualized by autoradiography. Position of RNA standards is indicated on the fight in kb. A transcript of approximately 2.5 kb was detected in all tissues with the possible exception of peripheral blood leukocytes (lane 9). Expression was evident in testis upon longer exposure of the blot to film.

Figure 9:
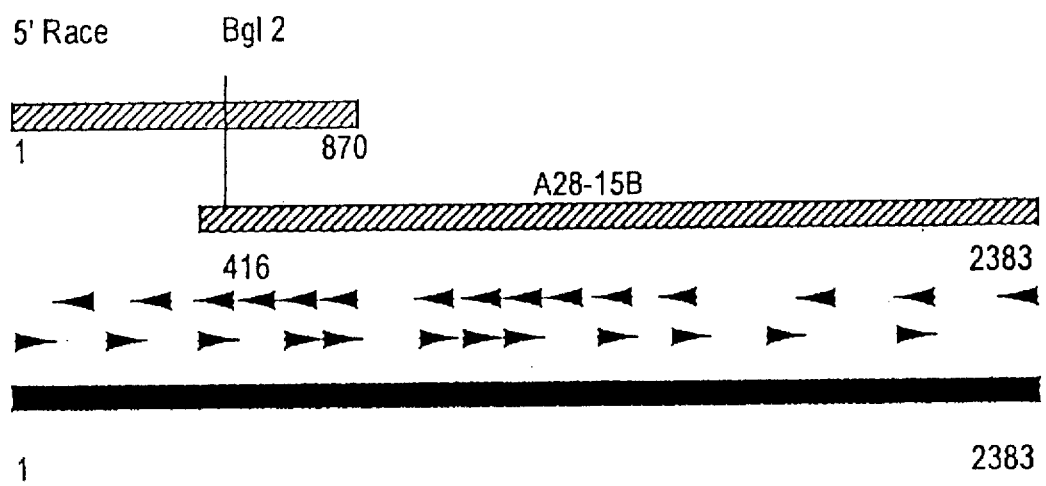

FIG. 9. Schematic representation of the cloning and sequencing strategy for the A28 cDNA encoding p53 response protein PIGI-1.

Human lung and brain cDNA libraries were screened with the A28 cDNA fragment identified in the library subtraction procedure. The longest hybridizing cDNA clone identified, A28-15B, was 1968 bp long and represented a partial cDNA clone. The 5' end of the cDNA was obtained by 5' RACE. The full-length (or near full-length) clone was assembled using the unique Bgl II site at nt position 416. The cDNA was sequenced in both directions using the gene specific oligonucleotides indicated and automated dye-deoxy nucleotide sequencing (ABI, Foster City, Calif.).

Figure 10:
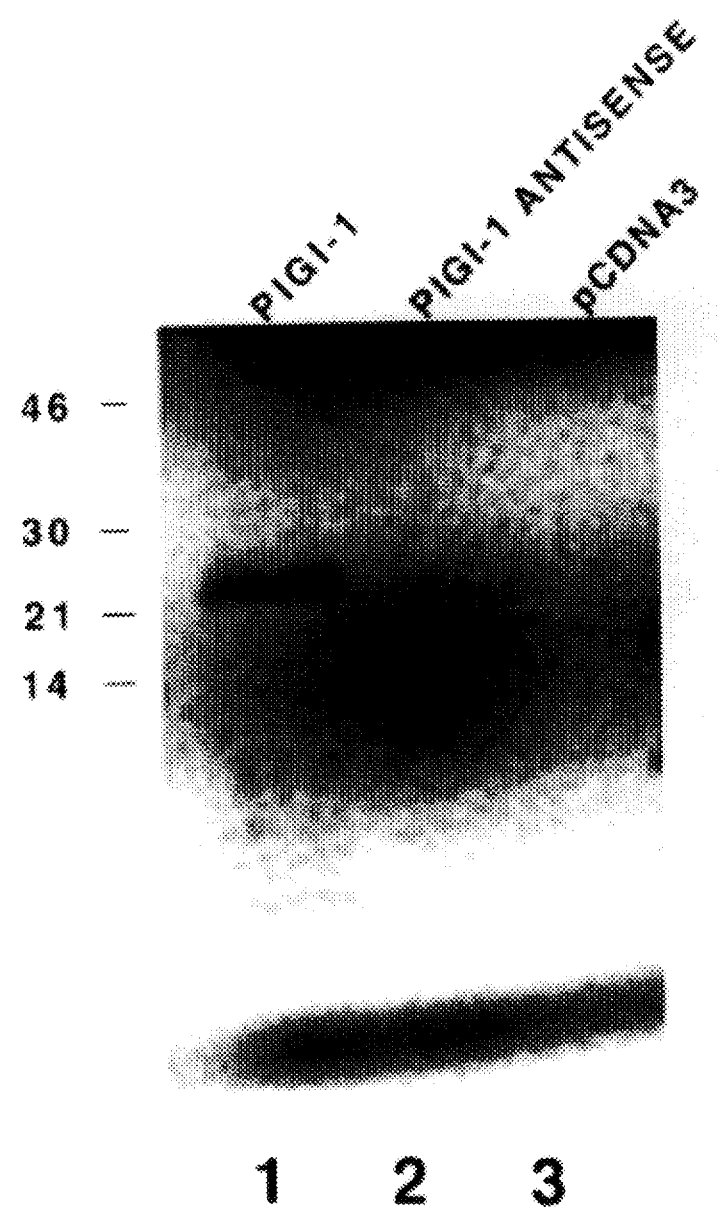

FIG. 10. In vitro translation of PIGI-1 protein.

DETAILED DESCRIPTION OF THE INVENTION

Use and utility

The nucleic acids of the present invention can be used in a variety of ways in accordance with the present invention. For example, they can be used as DNA probes to screen other cDNA and genomic DNA libraries so as to select by hybridization other DNA sequences that code for proteins related to p53 response protein PIGI-1. In addition, the nucleic acids of the present invention coding for all or part of p53 response protein PIGI-1 can be used as DNA probes to screen other cDNA and genomic DNA libraries to select by hybridization DNA sequences that code for p53 response protein PIGI-1 from other organisms. The nucleic acid probe could be RNA or DNA labeled with radioactive nucleotides or by non-radioactive methods (i.e., biotin). Screening could be done at various stringencies (through manipulation of the hybridization Tm, usually using a combination of ionic strength, temperature and/or presence of formamide) to isolate close or distantly related homologs. The nucleic acids may also be used to generate primers to amplify cDNA or genomic DNA using polymerase chain reaction (PCR) techniques. The nucleic acid sequences of the present invention can also be used to identify adjacent sequences in the cDNA or genome, for example, flanking sequences and regulatory elements.

The nucleic acid sequences of the present invention can also be used diagnostically to detect nucleic acid sequences encoding functionally compromised p53 response protein PIGI-1 in human tumors. This would be indicated by mutations, deletions or point mutations, which might be useful for diagnosis of cancers. Detection of such mutations could be determined by standard DNA analysis techniques, including genomic and/or cDNA sequencing, SSCP and Southern blot. In addition, functionally compromised p53 response protein PIGI-1 itself can be detected using monoclonal and polyclonal antibodies that can be generated to be selective for normal and mutant proteins using ELISA, immunoprecipitation, immunohistochemistry, or Western blot analysis.

The polypeptides of the present invention are useful in the study of the characteristics of p53 response protein PIGI-1; for example, its structure, mechanism of action, and role in oncogenesis. For example, PIGI-1 protein can be studied to further delineate its functional domains, and thus can be used to model compounds with similar activity. In addition, PIGI-1 protein can be utilized to determine if it interacts with itself, other related homologs, or other proteins using co-immunoprecipitation from labeled cell extracts, Western blotting, expression library screening using labeled PIGI-1 protein and/or other common methodologies. PIGI-1 protein can also be utilized to determine its ability to bind to DNA, and to identify its binding sites using screening of genomic sequence fragments or synthetic oligonucleotide fragments using a PCR-based technology of enrichment and amplification of selected DNA elements, which themselves may be targets for drug discovery efforts. PIGI-1 protein can also be used in in vivo cell based and in vitro cell free assays to screen natural products and synthetic compounds which might mimic, regulate or stimulate PIGI-1 protein function. PIGI-1 expression (either RNA or protein product) can be used to monitor the presence of wild-type p53 activity, as in screening for compounds which mimic or restore function to mutant p53.

As indicated hereinbelow, PIGI-1 protein possesses growth inhibitor properties, and may be functionally compromised in human tumors. Thus, various PIGI-1 protein targeted therapies may be utilized in treating tumors and cancer. For example, gene therapy techniques utilizing all or part of the nucleic acid sequences encoding PIGI-1 protein, techniques involving administration of PIGI-1 protein or biologically active fragments thereof, techniques utilizing antigen-specific antibodies fused to PIGI-1 protein or biologically active fragments thereof, or techniques utilizing small molecules or compounds modeled or discovered to mimic PIGI-1 may be used in treating tumors and cancer.

Various other methods of using the nucleic acids, polypeptides, expression vectors and host cells of the present invention are described in detail below.
Nucleic acids The present invention concerns an isolated nucleic acid molecule comprising a nucleic acid sequence coding for all or part of p53 response protein PIGI-1. Preferably, the nucleic acid molecule is a DNA molecule and the nucleic acid sequence is a DNA sequence. Further preferred is a DNA sequence having all or part of the nucleotide sequence as shown in FIG. 6 [SEQ ID NO: 1]. Also preferred are nucleic acid sequences complementary to one of these nucleic acid sequences. Additionally preferred are nucleic acid sequences which hybridize to one of these nucleic acid sequences. In the case of a nucleotide sequence (e.g., a DNA sequence) coding for part of p53 response protein PIGI-1, it is preferred that the nucleotide sequence be at least about 15 sequential nucleotides in length, more preferably at least about 20 to 30 sequential nucleotides in length.

The nucleic acids of the present invention can be isolated from a variety of sources, although the presently preferred sequences have been isolated from human cDNA libraries. The exact amino acid sequence of the polypeptide molecule produced will vary with the initial DNA sequence.

The nucleic acids of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;
(2) the chemical synthesis of the DNA sequence; and
(3) the synthesis of the DNA sequence by polymerase chain reaction (PCR).

In the first method, a genomic or cDNA library can be screened in order to identify a DNA sequence coding for all or part of p53 response protein PIGI-1. For example, human cDNA libraries can be screened in order to identify a DNA sequence coding for all or part of p53 response protein PIGI-1. Various cDNA libraries, for example, human adult lung and human adult brain (striata) cDNA libraries (Stratagene, La Jolla, Calif.), can be used.

Various techniques can be used to screen genomic DNA or cDNA libraries for sequences that code for novel p53 response protein PIGI-1. This technique may, for example, employ a labeled single-stranded DNA probe with a sequence complementary to a sequence that codes for p53 response protein PIGI-1. For example, DNA/DNA hybridization procedures may be used to identify the sequence in cloned copies of genomic DNA or cDNA which have been denatured to a single-stranded form. Suitable probes include cDNA for p53 response protein PIGI-1 acquired from the same or a related species, synthetic oligonucleotides, and the like.

A genomic DNA or cDNA library can also be screened for a genomic DNA or cDNA coding for all or part of p53 response protein PIGI-1, and for sequences flanking such coding sequences, using immunoblotting techniques.

In one typical screening method suitable for the hybridization techniques, a genomic DNA or cDNA library is first spread out on agar plates, and then the clones are transferred to filter membranes, for example, nitrocellulose membranes. The genomic library is usually contained in a vector such as EMBL 3 or EMBL 4 or derivatives thereof(e.g., lambda DASH™), or in cosmid libraries, P1 phage libraries or YAC libraries. The cDNA library is usually contained in a vector such as lgt10, lgt11, or lambda ZAP. A DNA probe can then be hybridized to the clones to identify those clones containing the genomic DNA or cDNA coding for all or part of p53 response protein PIGI-1. Alternatively, appropriate *E. coli* strains containing vectors such as lgt11 or lambda ZAP can be induced to synthesize fusion proteins containing fragments of proteins corresponding to the cDNA insert in the vector. The fusion proteins may be transferred to filter membranes, for example, nitrocellulose. An antibody may then be bound to the fusion protein to identify all or part of p53 response protein PIGI-1.

In the second method, the nucleic acids of the present invention coding for all or part of p53 response protein PIGI-1 can be chemically synthesized. Shorter oligonucleotides, such as 15 to 50 nucleotides, may be directly synthesized. For longer oligonucleotides, the DNA sequence coding for p53 response protein PIGI-1 can be synthesized as a series of 50–100 base oligonucleotides that can then be sequentially ligated (via appropriate terminal restriction sites) so as to form the correct linear sequence of nucleotides.

In the third method, the nucleic acids of the present invention coding for all or part of p53 response protein PIGI-1 can be synthesized using PCR. Briefly, pairs of synthetic DNA oligonucleotides generally at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the PCR primers. See White, T. J. et al., Trends Genet. 5, 185–9 (1989).

The nucleic acids of the present invention coding for all or part of p53 response protein PIGI-1 can also be modified (i.e., mutated) to prepare various mutations. Such mutations may change the amino acid sequence encoded by the mutated codon, or they may be silent and not change the amino acid sequence. These modified nucleic acids may be prepared, for example, by mutating the nueleic acid coding for p53 response protein PIGI-1 so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–64 (1985)and Kunkel, J. A., Proc. Natl. Acad. Sci. U.S.A. 82, 482–92 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers, J. R. et al., Nucl. Acids Res. 16, 791–800 (1988) may also be employed. Mutations may be advantageous in producing or using the polypeptides of the present invention. For example, these mutations may modify the function of the protein (e.g., result in higher or lower activity), permit higher levels of protein production or easier purification of the protein, or provide additional restriction endonuclease recognition sites in the nucleic acid. All such modified nucleic acids and polypeptide molecules are included within the scope of the present invention.

As used in the present application, unless otherwise limited in specific instances, the term "modified", when referring to a nucleotide or polypeptide sequence, means a nucleotide or polypeptide sequence which differs from the wild-type sequence found in nature.

Expression vectors

The present invention further concerns expression vectors comprising a DNA sequence coding for all or part of p53 response protein PIGI-1. The expression vectors preferably contain all or part of the DNA sequence having the nucleotide sequence shown in FIG. 6 [SEQ ID NO: 1 ]. Further preferred are expression vectors comprising one or more regulatory DNA sequences operatively linked to the DNA sequence coding for all or part of p53 response protein PIGI-1. As used in this context, the term "operatively linked" means that the regulatory DNA sequences are capable of directing the replication and/or the expression of the DNA sequence coding for all or part of p53 response protein PIGI-1.

Expression vectors of utility in the present invention are often in the form of "plasmids", which refer to circular double stranded DNA loops that, in their vector form, are not bound to the chromosome. However, the invention is intended to include such other forms of expression vectors which serve equivalent functions and which become known in the art subsequently hereto. The expression vectors of the present invention may also be used to stably integrate the DNA sequence encoding p53 response protein PIGI-1 into the chromosome of an appropriate host cell (e.g.,COS, HepG2, Saos 2 and EB cells).

Expression vectors useful in the present invention typically contain an origin of replication, a promoter located 5' to (i.e., upstream of) and followed by the DNA sequence coding for all or part of p53 response protein PIGI-1, transcription termination sequences, and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, sequences which provide sites for cleavage by restriction endonucleases, and sequences which allow expression in various types of hosts, including but not limited to prokaryotes, yeasts, fungi, plants and higher eukaryotes. The characteristics of the actual expression vector used must be compatible with the host cell which is to be employed. For example, when expressing DNA sequences in a mammalian cell system, the expression vector should contain promoters isolated from the genome of mammalian cells, (e.g., mouse metallothionein promoter), or from viruses that grow in these cells (e.g., vaccinia virus 7.5 K promoter). An expression vector as contemplated by the present invention is at least capable of directing the replication, and preferably the expression, of the nucleic acids of the present invention. Suitable origins of replication include, for example, the Col E1, the SV40 viral and the M13 orgins of replication. Suitable promoters include, for example, the cytomegalovirus promoter, the lac Z promoter, the gal 10 promoter and the Autographa californica multiple nuclear polyhedrosis virus (AcMNPV) polyhedral promoter. Suitable termination sequences include, for example, the bovine growth hormone, SV40, lac Z and AcMNPV polyhedral polyadenylation signals. Examples of selectable markers include neomycin, ampicillin, and hygromycin resistance and the like. All of these materials are known in the art and are commercially available.

Suitable commercially available expression vectors into which the DNA sequences of the present invention may be inserted include the mammalian expression vectors pcDNA3 or pcDNA/Neo, the baculovirus expression vectors pBlueBac and BlueBacHis, the prokaryotic expression vector pcDNAII and the yeast expression vector pYes2, all of which may be obtained from Invitrogen Corp., San Diego, Calif.

Suitable expression vectors containing the desired coding and control regions may be constructed using standard recombinant DNA techniques known in the art, many of which are described in Sambrook, et al., Molecular Cloning: A Laboratory Manual, Second Edition, Cold Spring Harbor Laboratory, Cold Spring Habor, N.Y. (1989).

As used in the present application, unless otherwise limited in specific instances, the phrase "control regions" refers to nucleotide sequences that regulate expression of p53 response protein PIGI-1, including but not limited to any promoter, silencer, enhancer elements, splice sites, transcriptional initiation elements, transcriptional termination elements, polyadenylation signals, translational control elements, translational start site, translational termination sites, and message stability elements. Such control regions may be located in sequences 5' or 3' to the coding region or in introns interrupting the coding region.

Host cells

The present invention additionally concerns host cells containing an expression vector which comprises a DNA sequence coding for all or part of p53 response protein PIGI-1. See, for example, the host cells of Example 2 hereinbelow, which are preferred. The host cells preferably contain an expression vector which comprises all or part of the DNA sequence having the nucleotide sequence substantially as shown in FIG. 6. See, for example, the expression vector appearing in Example 2 hereinbelow, which is preferred. Further preferred are host cells containing an expression vector comprising one or more regulatory DNA sequences capable of directing the replication and/or the expression of and operatively linked to a DNA sequence coding for all or part of p53 response protein PIGI-1. Suitable host cells include both prokaryotic and eukaryotic cells. Suitable prokaryotic host cells include, for example, *E. coli* strains HB101, DH5a, XL1 Blue, Y1090 and JM101. Suitable eukaryotic host cells include, for example, *Spodoptera frugiperda* insect cells, COS-7 cells, Saos-2 cells, HeLa cells, human skin fibroblasts, and *Saccharomyces cerevisiae* cells.

Expression vectors may be introduced into host cells by various methods known in the art. For example, transfection of host cells with expression vectors can be carried out by the calcium phosphate precipitation method. However, other methods for introducing expression vectors into host cells, for example, electropotation, liposomal fusion, nuclear injection, and vital or phage infection can also be employed.

Once an expression vector has been introduced into an appropriate host cell, the host cell may be cultured under conditions permitting expression of large amounts of the desired polypeptide, in this case a polypeptide molecule comprising all or part of p53 response protein PIGI-1.

Host cells containing an expression vector that contains a DNA sequence coding for all or part of p53 response protein PIGI-1 may be identified by one or more of the following six general approaches: (a) DNA-DNA hybridization; (b) the presence or absence of marker gene functions; (c) assessing the level of transcription as measured by the production of mRNA transcripts encoding p53 response protein PIGI-1 in the host cell; (d) detection of the gene product immunologically; (e) biological activity; and (f) PCR.

In the first approach, the presence of a DNA sequence coding for all or part of p53 response protein PIGI-1 can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, etc.). A marker gene can be placed in the same plasmid as the DNA sequence coding for all or part of p53 response protein PIGI-1 under the regulation of the same or a different promoter used to regulate the p53 response protein PIGI-1 coding sequence. Expression of the marker gene indicates expression of the DNA sequence coding for all or part of p53 response protein PIGI-1.

In the third approach, the production of mRNA transcripts encoding p53 response protein PIGI-1 can be assessed by hybridization assays. For example, polyadenylated RNA can be isolated and analyzed by Northern blotting or a nuclease protection assay using a probe complementary to the RNA sequence. Alternatively, the total RNA of the host cell may be extracted and assayed for hybridization to such probes.

In the fourth approach, the expression of all or part of p53 response protein PIGI-1 can be assessed immunologically, for example, by immunoblotting with antibody to p53 response protein PIGI-1 (Western blotting).

In the fifth approach, expression of p53 response protein PIGI-1 can be measured by assaying for p53 response protein PIGI-1 activity using known methods.

In the sixth approach, oligonucleotide primers homologous to sequences present in the expression system (i.e., expression vector sequences or p53 response protein PIGI-1 sequences) are used in a PCR to produce a DNA fragment of predicted length, indicating incorporation of the expression system in the host cell.

The DNA sequences of expression vectors, plasmids or DNA molecules of the present invention may be determined by various methods known in the art. For example, the dideoxy chain termination method as described in Sanger et al., Proc. Natl. Acad. Sci. U.S.A. 74, 5463–7 (1977), or the Maxam-Gilbert method as described in Proc. Natl. Acad. Sci. U.S.A. 74, 560–4 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

Polypeptides

The present invention further concerns polypeptide molecules comprising all or part of p53 response protein PIGI-1, said polypeptide molecules preferably having all or part of the amino acid sequence as shown in FIG. 7 [SEQ ID NO: 2]. In the case of polypeptide molecules comprising part of p53 response protein PIGI-1, it is preferred that polypeptide molecules be at least about 5 to 8 sequential amino acids in length, more preferably at least about 15 to 20 sequential amino acids in length.

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described by Houghton et al., Proc. Natl. Acad. Sci. 82, 5131–5135 (1985) may be employed. It is preferred that the polypeptides be obtained by production in prokaryotic or eukaryotic host cells expressing a DNA sequence coding for all or part of p53 response protein PIGI-1, or by in vitro translation of the mRNA encoded by a DNA sequence coding for all or part of p53 response protein PIGI-1. For example, the DNA sequence of FIG. 6 [SEQ ID NO: 1] may be synthesized using PCR as described above and inserted into a suitable expression vector, which in turn may be used to transform a suitable host cell. The recombinant host cell may then be cultured to produce p53 response protein PIGI-1. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides, even those which are biologically inactive, may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay, enzyme immunoassay, or immunocytochemistry. The antibodies may also be used in affinity chromatography for isolating or purifying the polypeptides of the present invention from various sources.

The polypeptides of the present invention have been defined by means of determined DNA and deduced amino acid sequencing. Due to the degeneracy of the genetic code, other DNA sequences which encode the same amino acid sequence depicted in FIG. 7 [SEQ ID NO:2], or any part thereof may be used for the production of the polypeptides of the present invention.

It should be further understood that allelic variations of these DNA and amino acid sequences naturally exist, or may be intentionally introduced using methods known in the art. These variations may be demonstrated by one or more amino acid changes in the overall sequence, such as deletions, substitutions, insertions, inversions or addition of one or more amino acids in said sequence. Such changes may be advantageous in producing or using the polypeptides of the present invention; for example in isolation of p53 response protein PIGI-1 or the polypeptides by affinity purification. Amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leueine, isoleueine, valine, glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formyimethionine and leader sequences. All such variations are included within the scope of the present invention.

Method for detection of nucleic acids

The present invention further concerns a method for detecting a nucleic acid sequence coding for all or part of p53 response protein PIGI-1 or a related nucleic acid sequence, comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in FIG. 6 [SEQ ID NO:1 ], or is complementary thereto.

A DNA sample containing the DNA sequence can be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and SDS, and incubating the resulting solution until most of the cellular protein is degraded. The genomic DNA is then deproteinized by successive phenol/chloroform/isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of medium and then lysing the cells by placing them in a 4 M guanidinium solution. The viscosity of the resulting solution is reduced by drawing the lysate through a 20-gauge needle. The RNA is then pelleted through a cesium chloride step gradient, and the supernatant fluid from the gradient carefully removed to allow complete separation of the RNA, found in the pellet, from contaminating DNA and protein.

The detectable marker useful for detecting a nucleic acid sequence coding for all or part of p53 response protein PIGI-1 or a related nucleic acid sequence, may be a labeled DNA sequence, including a labeled cDNA sequence, having a nucleotide sequence complementary to at least a portion of the nucleic acid sequence coding for all or part of p53 response protein PIGI-1.

The detectable marker may also be a labeled RNA having a sequence complementary to at least a portion of the DNA sequence coding for all or part of p53 response protein PIGI-1.

The detectable markers of the present invention may be labeled with commonly employed radioactive labels, such as $^{32}$p and $^{35}$S, although other labels such as biotin or mercury may be employed. Various methods well-known to those of ordinary skill in the art may be used to label the detectable markers. For example, DNA sequences and RNA sequences may be labeled with $^{32}$p or $^{35}$S using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for all or part of p53 response protein PIGI-1 in genomic DNA, the genomic DNA is first isolated using known methods, and then digested with one or more restriction enzymes. The resulting DNA fragments are separated on agarose gels, denatured in situ, and transferred to membrane filters. After prehybridization to reduce nonspecific hybridization, a radiolabeled nucleic acid probe is hybridized to the immobilized DNA fragments. The membrane is then washed to remove unbound or weakly bound probe, and is then autoradiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for all or pan of p53 response protein PIGI-1 can also be detected using the methods described herein. For example, a DNA probe that has conserved regions of the gene for a novel p53 response protein can be used to detect and isolate related DNA sequences (e.g., a DNA sequence coding for a response protein related to p53 response protein PIGI-1 from mice, rats, hamsters, or dogs). PIGI-1 cDNA can also be used to isolate flanking regulatory regions such as promoters, and to isolate novel genes which by their proximity may also be regulated by p53. All such methods are included within the scope of the present invention.

As used in the present application, unless otherwise limited in specific instances, the term "related", when refer-

13 ring to a nucleotide sequence, means a nucleic acid sequence which is able to hybridize to an oligonucleotide probe based on the nucleotide sequence encoding p53 response protein PIGI-1.

The following examples further illustrate the present invention. These examples are not intended to limit the scope of the present invention, and may provide further understanding of the invention.

EXAMPLE I

Identification of Novel p53 Response Genes

A. MATERIALS AND METHODS

1. Plasmid Construction:

Plasmids pUHD15-1 Neo (Tet-Vp 16 fusion-protein expression construct), pUHC13-3 (Tet-VP16 responsive luciferase construct, contains TET-operator sequences), and pUHG10-3 (Tet-Vp 16 responsive expression vector), were obtained from Dr. H. Bujard, University of Heidelberg, Heidelberg, Germay. The cDNA encoding p53 mutant at codon 143 (V to A substitution) was subcloned from plasmid pC53-SCX3 [Baker, S. J. et al, Science 249, 912–915 (1990)] into the BamHI site of pUHG10-3 giving rise to pTE9.5. pTE3.1 was constructed by subcloning the cDNA encoding p53 mutant at codon 247 (N to I substitution) from plasmid Gal4-53 247 [Unger, T. et al, EMBO J. 11, 1383–1390 (1992)] into pUHG10-3. The p53 responsive luciferase reporter construct was generated by replacing the TET-operator sequences of pUHC13-3 with two copies of a DNA fragment, 5'-TCGAGCTTGCCTGGACTTGCCTGCCAGATCTGTCGA CGGAGG-3'[SEQ ID NO: 3], containing the RGC p53 binding site [Kern, S. E. et al, Science 252, 1708–1711 (1991)], yielding plasmid mRE10. All recombinant o constructs were characterized and confirmed by sequence analysis using automated DNA sequencing (Applied Biosystems, Inc., Foster City, Calif.).

2. Development of p53 expressing cell lines:

Saos-2 cells (American Type Cell Culture, Bethesda, Md.) were grown at 37° C., 5% $CO_2$, in McCoys media supplemented with 15% fetal calf serum, 2 mM L-Glutamine, and 10 U Penicillin, 10 ug/ml streptomycin (Gibco). Cells were co-transfected by electroporation (Gibco electroporator) with the tTa expression plasmid pUHD15-1Neo (providing resistance to G418) and either pTE9.5 or pTE3.1 (at a 1:10 ratio, respectively). Cells were selected in media containing G418 (250 u/ml, Gibco) and tetracycline ( 1 ug/ml, Sigma). G418-resistant colonies were cloned and expanded, yielding Saos-2-A3 and Saos-2-D4.

Derivatives of Saos-2-A3 and Saos-2-D4 containing the luciferase reporter construct mRE10, were subsequently established using pBShygro for positive selection (expresses the bacterial hygromycin resistance gene under control of the SV40 early promoter, obtained from Dr. Mark Lynch, Bristol-Myers Squibb) of resistant cells in media containing hygromycin B (150 U/ml), yielding clonal lines Saos-2-A3B and Saos-2-D4H, respectively. EB and clonal EB1 cells obtained from P. Shaw [Shaw, P. et al, Proc. Natl. Acad. Sci. U.S.A. 89, 4495–4499 (1992)] were maintained at 37° C. and 9% $CO_2$ in DMEM (Gibco) supplemented with 10% fetal calf serum and antibiotics as described above.

3. Luciferase assay:

Cell extracts were prepared in 100 ul of 2× luciferase buffer (30 mM glycylglycine pH 7.8, 30 mM $MgSO_4$, 1.0 mM EGTA [Ethylene Glycol-bis(B-aminoethyl Ether)N,N, N',N'-tetraacetic acid], 2.0 mM DTT [dithiothreitol]) con-

14 taining 1% Triton X 100. Luciferase activity was determined by reading in a luminometer (Berthold model LB 952 T/16 or Dynatech model ML 1000) the relative luminescence produced by 50 ul of extract (corrected for protein concentration) following injection of 100 ul of assay buffer (1× luciferase buffer with 2.0 mM ATP [adenosine triphosphate, pH7.0] and 5 mM luciferin).

4. Isolation of RNA and Northern blot analysis:

Total RNA was prepared using the acid guanidinium thiocyanate single step isolation method [Chomczynski, P. et al, Anal. Biochem. 162, 156–159 (1987)]. Poly-adenylated RNA was prepared using oligotex dT (Qiagen). Northern blot analysis was as described previously [Buckbinder, L. et al, J. Biol. Chem. 267, 25786–25791 (1992)]. Quantitation of Northern blots was performed using laser densitometry (Molecular Dynamics) of the autoradiograms or by exposing the blots to phosphorimaging plates followed by analysis on a phosphoimager (Fuji).

5. cDNA libraries:

The cDNA library subtraction procedure was performed essentially as described [Wang, Z. et al, Proc. Natl. Acad. Sci. U.S.A. 88, 11505–11509 (1991)], except where noted below. cDNA was divided into three aliquots of which one was digested with Hae III and one with Rsa I. Linker addition, PCR amplification, preparation of biotinylated driver DNA, hybridization and hybrid removal were as described previously [Wang, Z. et al, Proc. Natl. Acad. Sci. U.S.A. 88, 11505–11509 (1991); Buckbinder, L. et al, J. Biol. Chem 267, 25786–25791 (1992)]. cDNA cloning and screening began after the third round of subtraction. The cloned cDNA fragment that was identified (W4.5) was then added to the driver to suppress the fragment so that different cDNAs could be enriched in a fourth-round screen.

6. Western blot analysis:

Nuclear proteins (80 ug) were resolved by SDS polyacrylamide gel electrophoresis (12%). Proteins were electroblotted to a PVDF membrane (Gibco) and immunoblot analysis performed as described by [Harlow, E. et al, Antibodies: A Laboratory Manual, Cold Spring Harbor Press (1988)]. p53 monoclonal antibody DO1 (mAB-6, Oncogene Science, Uniondale, N.Y.) was used as primary antibody. Western blot reactions were detected using a chemiluminescence-based photoblot system (Gibco, Grand Island, N.Y.). Quantitation of the autoradiogram was as described above.

B. Results

1. Development of cell lines carrying inducible p53 genes:

Saos-2 human osteosarcoma cells were chosen as the parental cell line for several reasons: 1) they are null for p53, 2) overexpression of exogenous wt p53 in these cells inhibits their growth [Diller, L. et at, Mol. Cell. Biol. 10, 5772–5781 (1990)], and 3) in transient expression assays, several temperature-sensitive (ts) mutants of human p53 activate, at the permissive temperature (30° C.), a reporter gene which has upstream p53-responsive elements (data not shown). Two naturally occurring mutants of p53 were chosen for establishing stable cell lines: p53N247I (asparagine to isoleucine substitution at codon 247) and p53V143A (valine to alanine substitution at codon 143). The p53N247I mutant was shown to display, as a GAL4-fusion protein, a ts-phenotype in transactivation [Unger, T., et at. EMBO J. 11, 1383–1390 (1992)]. The p53VI43A mutant [Baker, S. J. et at, Science 249, 912–915 (1990)] had not previously been characterized as a ts-mutant. However, DNA binding experiments with purified baculovirus p53V143A indicated that it binds effectively to DNA at 30° C. (Takenaka, Faha, and Kley, unpublished observation), and transient transfection experiments showed that it activated a p53-responsive reporter gene at the permissive temperature (data not shown).

2. Tetracycline-regulated p53 expression.

Figure 1A:
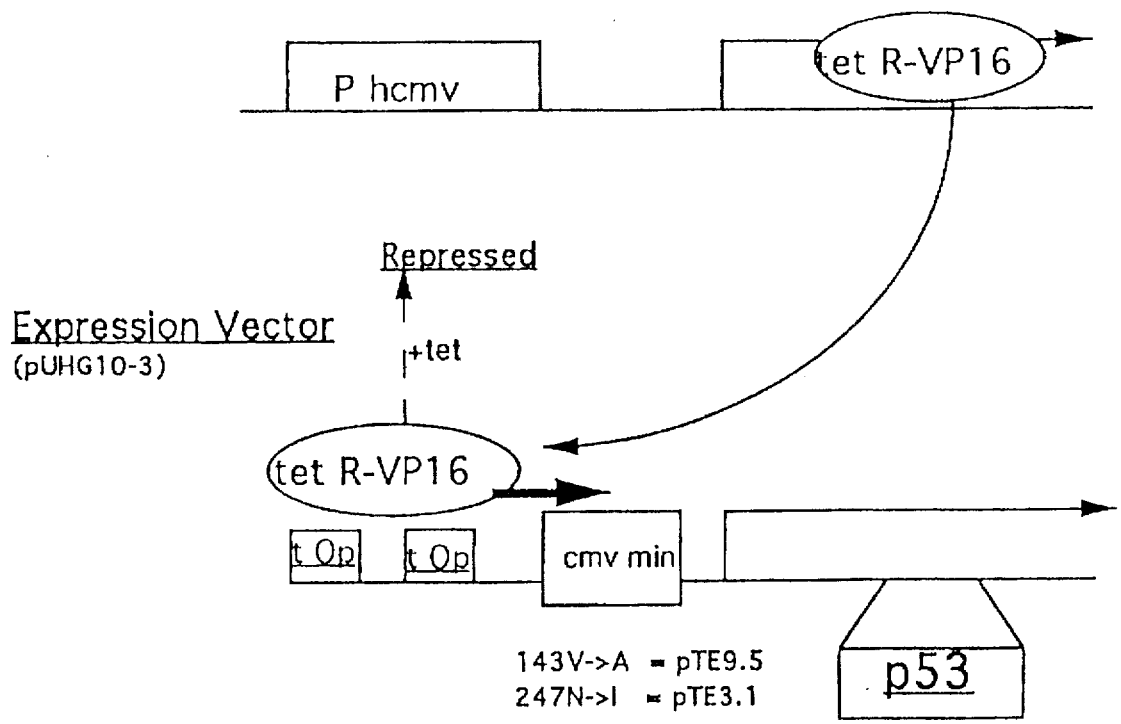
FIG. 1A. Plasmid constructs used for tet-regulated p53 expression. The tet-activator plasmid (pUHD 15-1 Neo) constitutively expresses tTa (see text). p53 mutants V143A and N247I were cloned into the tet-responsive expression vector pUHG 10-3, producing pTE9.5 and pTE3.1, respectively. Expression of the cloned p53 genes is regulated by tTa which binds to tOp in the absence of tetacycline and is repressed by tetracycline addition.
Figure 1B:
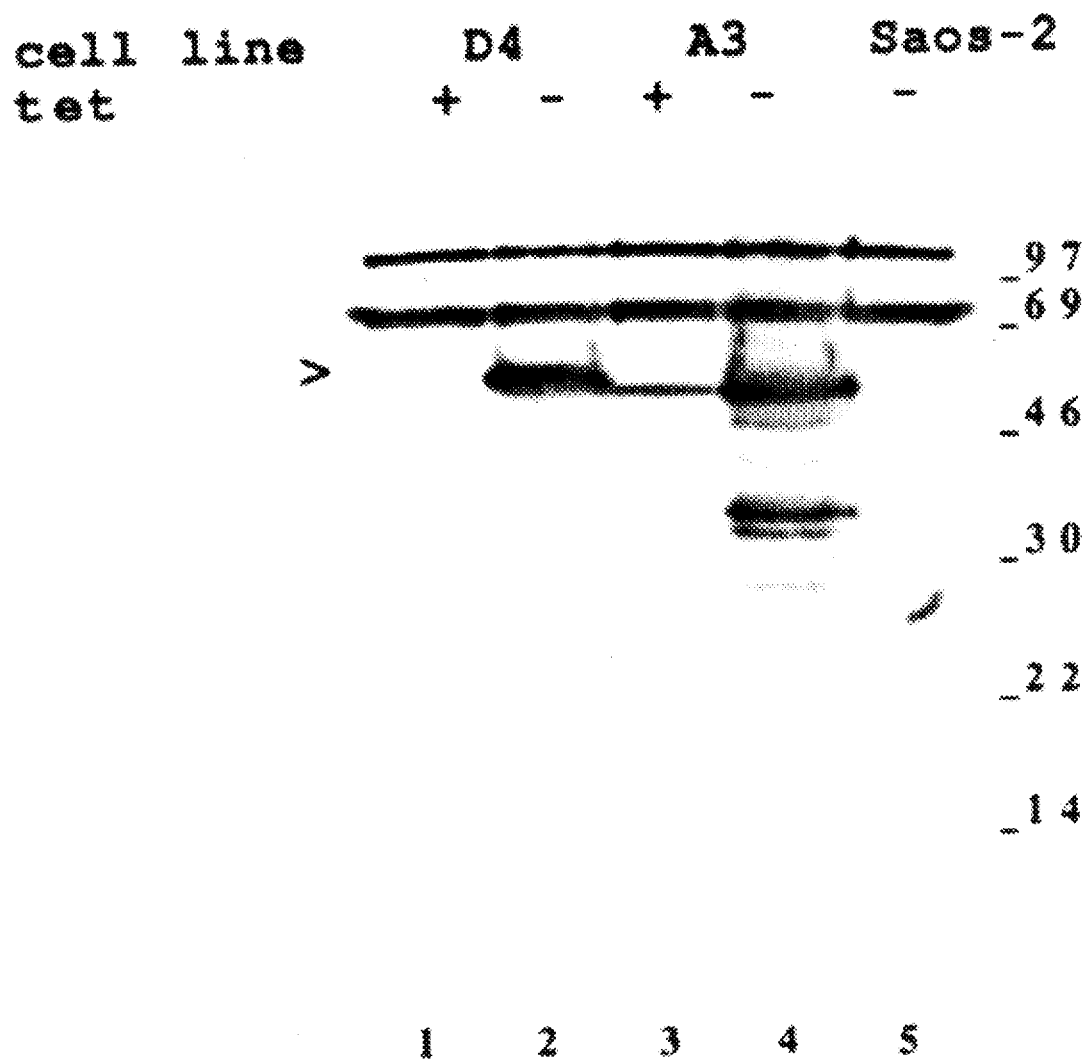
FIG. 1B. Western Blot analysis of p53 expression in Saos-2-A3 and -D4 cells. Parental Saos-2, Saos-2-D4 and -A3 cells were grown overnight with tetracycline (1 ug/ml) or without as indicated. Nuclear extracts were made the next day, 80 ug protein was resolved on an SDS polyacrylamide gel (12%), and p53 detected by Western blot analysis using the monoclonal antibody DO1 (Oncogene Science, Uniondale, N.Y.). Position of full-length p53 protein is marked by the arrowhead. Location of molecular weight standards is indicated on the right (in kilodaltons).

A tetracycline (tet)-regulated expression system established by Gossen and Bujard [Gossen, M. and Bujard, H., Proc. Natl. Acad. Sci. U.S.A. 89, 5547–5551 (1992)] was used to develop stable cell lines. The p53 cDNAs were cloned downstream of a minimal promoter carrying bacterial tet operator (tOp) sequences (see FIG. 1A). A CMV promoter drives constitutive expression of a bacterial tet-repressor-VP 16 (tTA) activator fusion protein which in the absence of tetracycline binds to tOp and activates transcription of the p53 expression construct. Addition of tetracycline inactivates tTA DNA binding, and thereby shuts down p53 expression. Thus, removal of tetracycline from the cell culture media results in a pronounced accumulation of p53 protein. Distinct clones Saos-2-A3 and Saos-2-D4, displaying tetracycline regulated expression of the two mutant p 53 proteins (p53N247I and p53V143A respectively) were selected for and expanded. FIG. 1B shows regulated expression of p53 in these cells at 37° C. upon removal of tetracycline from the culture media. Basal expression is practically undetectable in the Saos-2-D4 cell line. Induction of p53 is >20-fold in -D4H cells and ca. 5-fold in Saos-2-A3 cells (FIG. 1B), with the maximum induced levels of p53 being comparable in both cell lines (FIG. 1B).

3. Functional activity of ts p53 mutants.

Figure 2A:
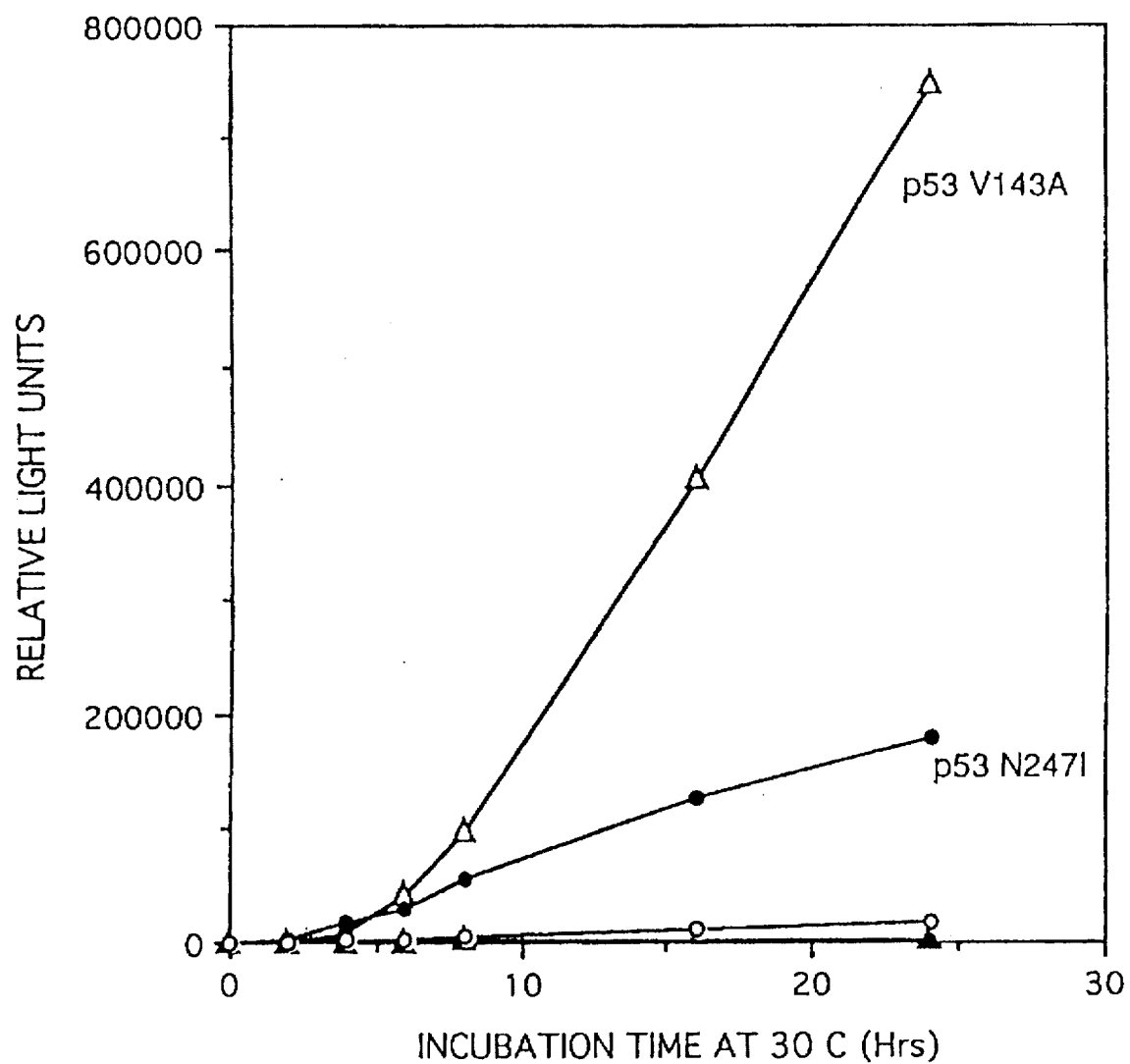
FIG. 2A. Induction of luciferase by temperature-reverted mutant p53 proteins. Sao-2-A3B and -D4H cells growing in tetracycline containing media were washed 4X with DMEM and incubated with antibiotic-free (● and ∆, respectively) or tetracycline-containing media (○ and ▲, 1 ug/ml, respectively). After 16 hours at 37° C., cells were switched to 30° C. (0 hrs time point). Cell extracts were prepared at the times indicated (in hours) and luciferase activity was determined using equal amounts of cell extracts.

Both the Saos-2-A3 and Saos-2-D4 cell lines were subsequently transfected with a luciferase reporter construct containing two copies of the RGC p53 binding sequences [Kern, S. E. et at, Science 252, 1708–1711 (1991)]. Stable clones carrying an integrated reporter construct, Saos-2-A3B and Saos-2-D4H, were selected for and characterized for p53-dependent luciferase induction. Luciferase expression was determined following shift to the permissive temperature (30° C.). Saos-2-A3B and -DH4 cells grown without tet showed strong induction upon incubation at 30° C. (FIG. 2A). Induction is rapid, yielding a 6 and 10 fold increase by 4 hrs, and a 10 and 200 fold induction by 24 hrs of incubation, in Saos-2-A3B and Saos-2-D4H cells respectively, indicating that these human ts mutant p53 proteins may indeed mimic the sequence specific transactivating functions of wt p53. No induction was detected in Saos-2-DH4 cells in the presence of tetracycline, and weak induction, probably due to a low basal p53 expression (FIG. 1B), was observed in Saos-2-A3B cells.

Figure 2B:
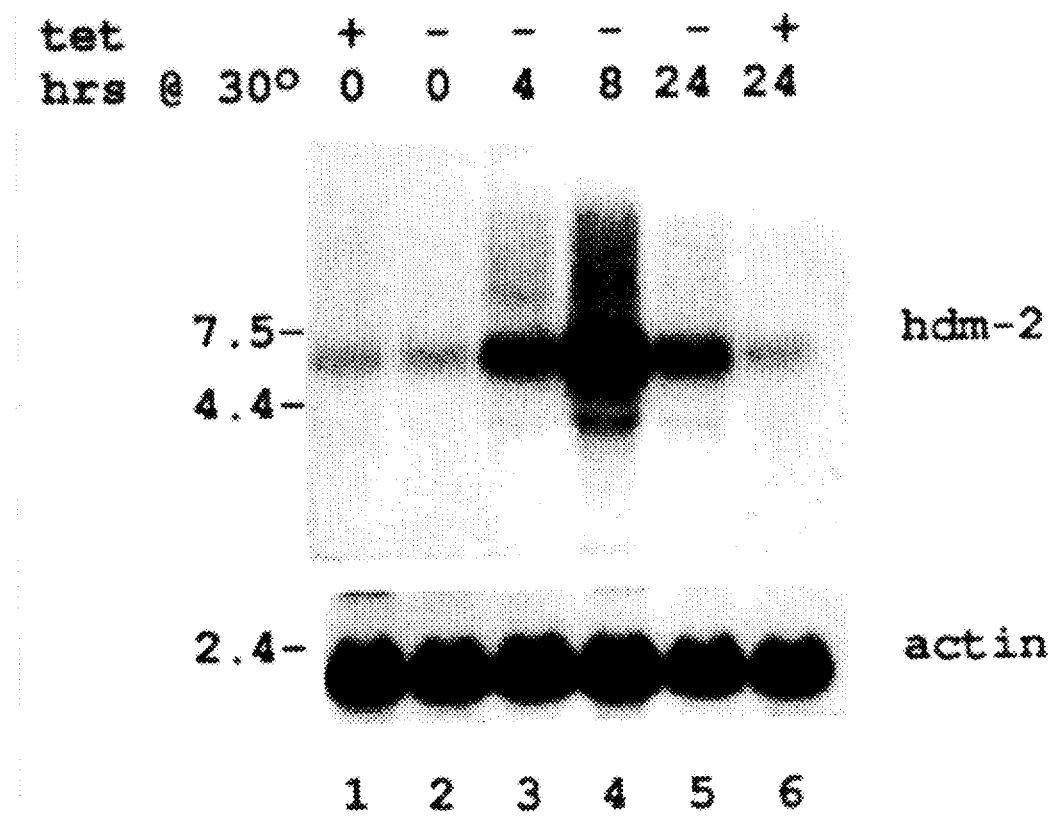
FIG. 2B. Induction of hdm-2 gene expression in Saos-2-D4H cells. Saos-2-D4H cells were grown overnight with tetracycline (1 ug/ml) or without and subsequently incubated at 30° C. for the time period indicated (in hours) before harvesting. Total RNA (10 ug) was analyzed by Northern blot analysis. Duplicate blots were hybridized with a $^{32}$P-labeled cDNA probe for either hdm-2 or β-actin, and autoradiograms of the hybridized blots are shown. Position of RNA molecular weight markers is indicated on the left.

Although these experiments showed that mutant p53 proteins, when reverted to a wt-like phenotype, can activate gene expression from an exogenous promoter carrying a p53 responsive element in an artificial context, it was unclear as to whether these mutant p53 proteins could actually activate endogenous gene expression. FIG. 2B shows that incubation of Saos-2-D4H cells (carrying the p53V143A mutant) at 30° C. is associated with a pronounced induction of the endogenous hdm-2 gene in a p53-dependent manner. RNA was prepared from -D4H cells that had been grown with or without tetracycline and incubated at 30° C. for various times, and characterized by Northern blot analysis. Induction of hdm-2 mRNA levels was maximal by 8 hrs after temperature-shift (10 fold, FIG. 2B). The subsequent, rapid decrease in hdm-2 mRNA levels may result, in part, from the rapid decrease in p53 expression occurring during this time period. p53 RNA levels decrease rapidly after temperature-shift to 30° C. (data not shown), which could be a result of the reduction in temperature and associated decrease in transcriptional activity, and/or some p53 mediated negative feedback effect.

4. Identification of novel p53-regulated genes:

Experiments described above suggested that the Saos-2-D4H cell line would represent a useful tool for the isolation of p53-regulated genes. To this end, RNA was prepared 8 hrs after temperature-shift from cells kept under three different conditions, referred to as: p53 "null" (incubated with tet at 30° C.), "wild-type" (incubated without tet at 30° C.), and "mutant" (incubated without tet and maintained at 37° C.). The methodology used to enrich for sequences induced by wild-type-like p53, i.e. temperature-reverted p53V143A, was based on a PCR driven library subtraction procedure [Wang, Z. et al, Proc. Nail Acad, Sci. U.S.A. 88, 11505–11509 (1991)] (see Materials and Methods hereinabove for details). Briefly, cDNA was prepared from the three RNA populations, digested with RsaI or HaeIII restriction enzymes, and following the addition of linkers amplified by PCR to give rise to the starting cDNA library material. Driver was prepared by coupling photobiotin to the "null" and "mutant" PCR fragments which were then incubated at 20 fold molar excess with "wild-type" fragments (tracer) in a hybridization mixture. After extended incubation, hybrids were removed and the remaining non-hybridized material subjected to a second cycle of hybridization. Non-hybridized material was PCR amplified to produce the first round enriched material. This was further enriched by two more cycles of driving. The up-regulated material was sufficiently enriched to be characterized by colony hybridization using the third round enriched probe.

5. Identification of intermediate-abundance class, p53-regulated transcripts.

Figure 3:
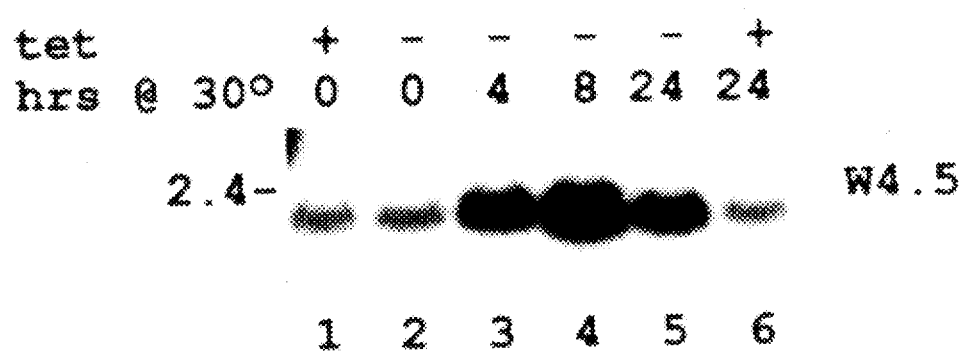
FIG. 3. Enriched cDNA fragment W4.5 identifies a p53-regulated transcript. Saos-2-D4H cells were incubated in the absence or presence of tetracycline (1 ug/ml) at 30° C. as described in FIG. 2B. A Northern blot (10 ug of total RNA/lane) was hybridized with a $^{32}$P-labeled cDNA probe corresponding to clone W4.5. Autoradiogram of the hybridized blot is shown with position of molecular weight marker indicated on the left.

All colonies that hybridized strongly with the third round enriched probe were composed of one cDNA fragment, called W4.5. Northern blot analysis using labeled W4.5 probe revealed a strongly hybridizing mRNA of ca. 2.2 kb in size present in "null" and "mutant" p53-expressing cells, and which was strongly induced upon shifting cells to the permissive temperature of 30° C. ("wild-type" status). 15-fold induction was achieved by 8 hrs following temperature-shift (FIG. 3). Similar to the profile observed for hdm-2 mRNA induction (see FIG. 2B), mRNA levels decreased thereafter. No DNA sequence homologics to W4.5 were initially detected by a search of the Genbank database. However, while we were characterizing this novel gene in more detail, a report [El Deiry, W. S. et al, Cell 75, 817–825 (1993)] appeared describing the identification of a p53-induced gene encoding a novel transcript of ca. 2.1 kb, called WAF1. Sequence comparison revealed that the DNA sequence of W4.5 is identical to that of a 466 bp RsaI restriction fragment present in the 3'-untranslated region of the published WAF1 cDNA sequence. Our independent cloning efforts confirm that WAF1 is a p53-regulated gene and show that it also is induced efficiently by a temperature-reverted human p53V143A mutant protein. Judging from the abundance of the W4.5 fragment in the original cDNA library starting material, and the intensity of the hybridizing mRNA species on Northern blots, relative to that of the β-actin mRNA transcript (high-abundance, ca. 0.5% of total mRNA population), the W.4.5 encoding transcript belongs to a class of intermediate-abundance class transcripts (0.1–0.05% of mRNA, based on comparison to β-actin).

The PCR-based library subtraction procedure tends to efficiently enrich for the most abundant and differentially expressed transcripts. In order to enrich for less abundant but regulated cDNA sequences, W4.5 fragments were driven out of the enriched cDNA library. This lead to the identification of two non-overlapping cDNA fragments, W5.5 and B26. Both W5.5 and B26 hybridized on Northern blots to a regulated transcript of ca. 6 kb in size (data not shown). Sequence analysis revealed that W5.5 is identical to a sequence present in the reported hdm-2 cDNA sequence. Sequence analysis of B26 did not reveal any sequence homology to the published, partial hdm-2 cDNA sequence. However, using genomic DNA from a human tumor previously characterized for amplification of the hdm-2 gene (obtained from A. J. Levine, Princeton University, Princeton, N.J.), we observed the presence of an amplified genomic DNA fragment upon Southern blot analysis. We conclude that B26 represents the second identified fragment for hdm-2 and most likely is encoded by untranslated regions within the gene that had not previously been cloned. Similar to the results obtained with the W4.5 probe, the hdm-2 transcript belongs to the intermediate-abundance class transcripts in these cells.

6. Identification of low-abundance class, novel p53-regulated transcripts.

After repeated library screening, single clones were identified for two non-overlapping cDNA fragments, A26 and A28. Upon hybridization to the starting material both fragments appeared to be encoded by low-abundance, but regulated transcripts. This was confirmed by Northern blot analysis. Due to the extremely low abundance of these transcripts (<0.005% of total mRNA, based on comparison to β-actin), poly-adenylated RNA was prepared from -DH4 cells grown in the absence of tetracycline and maintained at 37° C. or 30° C. for 7 hrs.

Figure 4:
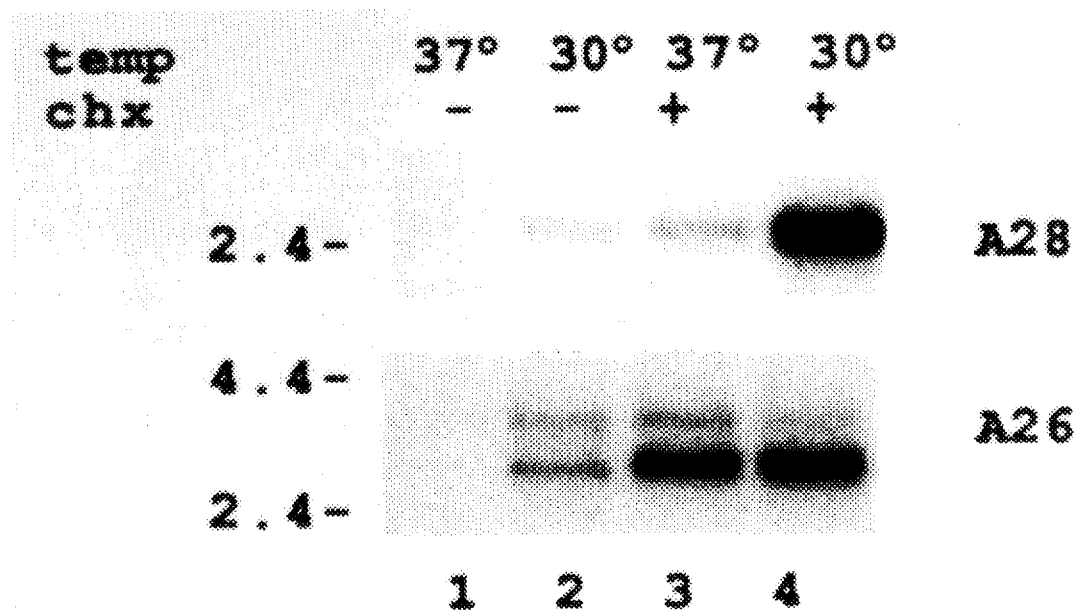
FIG. 4. Clones A28 and A26 identify transcripts regulated by the ts mutant p53V143A in Saos-2-D4H cells. Saos-2-D4H cells were grown in the absence of tetracycline at 37° C. Cells were treated with vehicle (water) or cycloheximide (10 ug/ml) for 30 minutes and subsequently incubated for 7 more hours at 37° or 30° C. as indicated. Northern blots were prepared using equal amounts of poly-adenylated RNA and hybridized sequentially with a $^{32}$P-labeled cDNA probe for A28 and A26. Autoradiograms are shown with the position of RNA molecular weight markers indicated on the left.

Northern blot analysis using probe A28 revealed a ca. 2.5 kb hybridizing mRNA that is induced upon temperature-shift in a p53-dependent manner (FIG. 4, lane 1 vs. 2). No induction was observed in the presence of tetracycline (data not shown). The size of the mRNA is distinct from other characterized p53-activated transcripts and appears to be encoded by a novel regulated gene. No sequence homologies were detected upon searching the Genbank database (data not shown). The gene encoding the A28 sequence appears to be a direct p53 response gene. This was examined in cells that were treated as before, except that the protein synthesis inhibitor cycloheximide (chx, 10 ug/ml) was added 30 min. prior to temperature-shift (chx treatment resulted in >95% inhibition of protein synthesis as judged by $^{35}S$ methionine labeling of cells, data not shown). Chx treatment increased the basal (non-induced) levels of the A28 encoded transcript but did not prevent p53-dependent induction of this transcript (12 fold induction, FIG. 4, lane 3 vs.4). Chx-mediated RNA stabilization, referred to as super-induction, has been observed for a number of RNA species and has been especially well characterized for the immediate-early serum response genes [Lau, L. F. and Nathans, D., (1991). Hormonal Control: Regulation of Gene Transcription (Cohen, P. and Fauiks, J. G. eds), pp 757–793, Elsevier Sciences Publishers, London]. As previously proposed, the lack of feedback inhibition or the turnover of labile inhibitors could account for this stabilization.

Probe A26 detected two RNA species of ca. 3 and 4 kb in size upon Northern blot analysis. Both RNA species are specifically induced in a p53-dependent manner upon temperature-shift of-D4H cells (5-fold, FIG. 4, lane 1 vs. 2). No induction was observed in the presence of tetracycline (data not shown). However, although regulated, it is unclear to date as to whether A26 is encoded by a direct p53 response gene. In chx-treated cells, the basal A26 encoding transcript is also increased, however, in contrast to the A28 encoded transcript, no induction was observed upon subsequent temperature-shift (FIG. 4, lane 3 vs. 4). Preliminary sequence information indicates that A26 is also encoded by a novel gene (data not shown).

7. Induction of novel p53-regulated transcripts correlates with p53-induced apoptosis.

Figure 5:
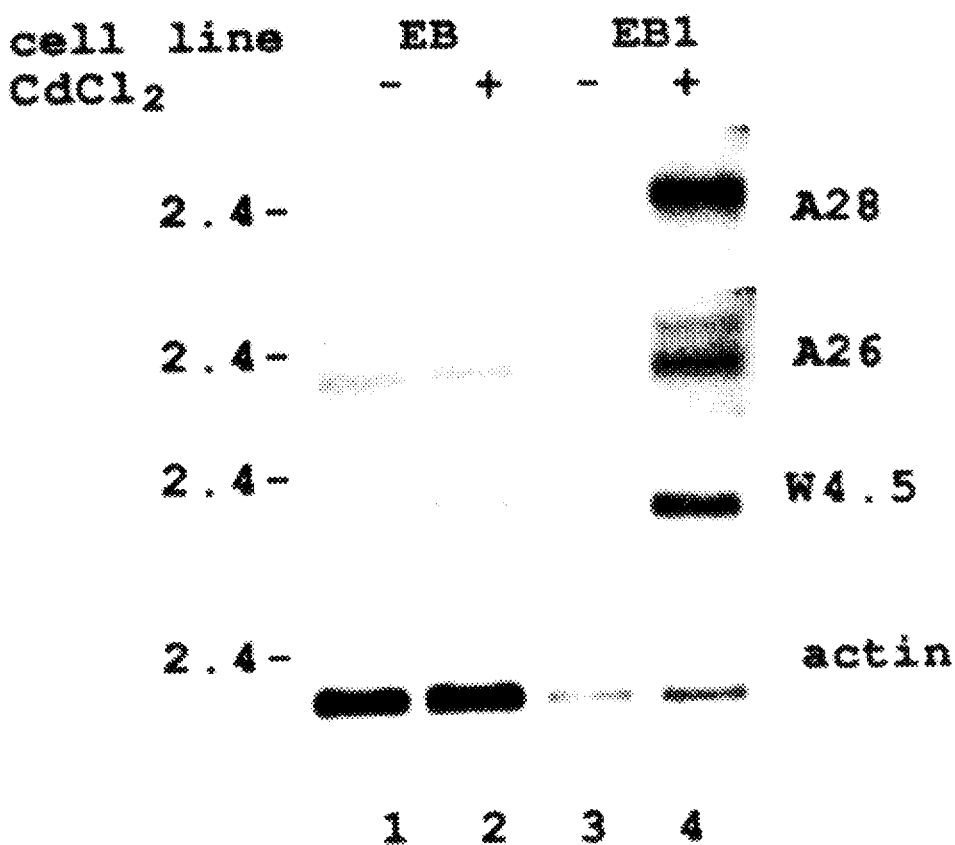
FIG. 5. A28 and A26 transcripts are induced by wild-type p53 in EB1 colon carcinoma cells.

To complement our studies on the regulation of the A28 and A26 encoding transcripts in Saos-2 cells, whose growth rate is reduced, but not abolished upon induction of wild-type like p53 as a consequence of temperature-shift (data not shown), we studied the regulation of these transcripts in a colorectal carcinoma cell line (EB) carrying an inducible wild-type p53 gene. In these EB cells, expression of wt p53 is placed under the control of a metallothionein promoter that is activated by metal ions such as zinc or cadmium [Shaw, P. et al, Proc. Natl. Acad. Sci. U.S.A. 89, 4495–4499 (1992)]. Expression of p53 in these cells, both in culture and as an established tumor in animals, leads to apoptosis [Shaw, P. et al, Proc. Natl. Acad. Sci. U.S.A. 89, 4495–4499 (1992)]. Poly-adenylated RNA was prepared from cultured parental EB and clonal EB1 cells (carrying the wt p53 gene) treated without or with cadmium (6 uM) for 10 hrs. Northern blot analysis shows that the transcript encoding A28 is strongly and specifically induced (>20- fold, FIG. 5) in cadmium-treated, p53-positive clonal EB1 cells. Similarly, transcripts hybridizing to probe A26 were induced (5-fold, FIG. 5). Interestingly, the major RNA species detected by the A26 probe are ca. 2 and 3 kb in size, as compared to ca. 3 and 4 kb for Saos-2-D4H cells. Upon longer exposure also a ca. 4 kb RNA species is detected (data not shown). One possible explanation for these findings is that the A26 encoding gene transcript is alternatively spliced in different cell types. WAF1/CIP1/p21 mRNA was induced 8-fold under these conditions (FIG. 5). Actin mRNA levels were not induced, and similar levels were observed in EB1 cells treated with or without cadmium (FIG. 5).

C. Discussion

The strong correlation between the ability of p53 to bind to DNA and activate transcription in a sequence-specific manner, and its ability to suppress cell growth or induce apoptosis, suggests that p53-induced genes may play a critical role in mediating the function of p53 as a tumor suppressor. In this study we set out to isolate and characterize such potential effectors in the p53 signaling pathway. This lead to the isolation of previously identified p53-regulated genes as well as additional, novel p53-regulated transcripts.

The strategy we used involved establishing genetically engineered human Saos-2 osteosarcoma cells (deficient in endogenous p53 expression) carrying inducible genes encoding temperature-sensitive (ts) mutants of p53. Using a tetracycline-regulated expression system, developed by Gossen and Bujard [Gossen, M. and Bujard, H., Proc. Natl. Acad. Sci. U.S.A. 89, 5547–5551 (1992)], stable cell lines containing an integrated p53 gene encoding either of two naturally occurring oncogenic mutants of p53, p53N247I and p53V143A, were established. p53 is tightly regulated by tetracycline, and upon temperature-shift ( 37° C. to 30° C.) both mutant proteins efficiently and specifically activate an integrated luciferase reporter construct containing two copies of the RGC p53-responsive element [Kern, S. E. et al, Science 252, 1708–1711 (1991)], and the endogenous hdm-2 gene. The p53N247I mutant has previously been shown to be temperature-sensitive for transactivation as a GAL4 fusion protein [Unger, T. et al, EMBO J. 11, 1383–1390 (1992)]. Our findings confirm that this mutant displays ts properties when expressed in a regulated fashion as a native protein. Furthermore, our studies reveal that the p53V143A mutant [Baker, S. J. et al, Science 249, 912–915 (1990)] is temperature-sensitive for transactivation and appears more active than the p53N247I mutant in these clonal Saos-2 cells. However, wild-type like activity was detected only upon incubation of cells at 30° C., as opposed to at 34° C. for the p53N247I mutant cells (data not shown). These results indicate that different p53 mutants may display different sensitivity with regard to their ability to revert to a wild-type like phenotype. Studies using purified baculovirus p53V143A show that this mutant is ts for DNA binding in vitro, indicating that temperature sensitivity is an intrinsic property of this p53 mutant (Takenaka, Faha, and Kley; unpublished observations).

Given its sensitivity to p53-dependent transactivation, the p53 V143A-expressing cell line, Saos-2-D4H, was used to isolate novel p53 up-regulated transcripts. The cDNAs we cloned using a selection procedure described by Wang and Brown [Wang, Z. and Brown, D. D., Proc. Natl. Acad. Sci. U.S.A. 88, 11505–11509 (1992)] are encoded by transcripts that pertain mainly to two categories, i.e. intermediate-abundance and low-abundance class p53-regulated transcripts (relative to the high abundance class β-actin transcript for instance). Clones we isolated for the intermediate-abundance class transcripts represented sequences encoded by the recently cloned WAF1/CIP1/p21 gene [El-Deiry, W. S. et al, Cell 75, 817–825 (1993)], reported during our characterization of the cloned W4.5 probe, and the hdm-2 gene. Thus, we independently confirmed that WAF1/CIP1/p21 is a p53-regulated gene, and demonstrate that its activation can be triggered by human, temperature-reverted mutant p53 proteins. This further confirms that these mutant proteins act as truly wild-type like p53 proteins at the permissive temperature. Clones we isolated for the low-abundance class transcripts (expression is at least one order of magnitude less than that for the WAF1/CIP1/p21 and hdm-2 transcripts) appear to be encoded by novel p53-regulated genes. One DNA fragment, A28, detects a p53-specific regulated mRNA of ca. 2.5 kb on Northern blots. Another cloned cDNA fragment, A26, detects two p53-specific up-regulated transcripts in Saos-2-D4H cells of ca. 3 kb and 4 kb in size.

Although both transcripts are regulated by p53, induction is distinct with regard to its sensitivity to the protein inhibitor cycloheximide. By definition the gene encoding A28 is a direct p53 response gene, as ongoing protein synthesis is not required for induction. In contrast, it is unclear as to whether the gene encoding A26 is a direct response gene as induction by p53 is blocked by cycloheximide. This may be interpreted in several ways: 1) the A26 encoding gene is not a direct response gene, 2) due to the stabilization of the A26 encoding RNA and possible activation of alternative signaling pathways upon treatment with cycloheximide, direct induction by p53 may be obscured, or 3) the kinetics of induction of the A26-encoding transcripts by p53 is comparable to that of other direct response genes such as WAF1/CIP1/p21, and hdm-2, suggesting that the A26 encoding gene may be a direct response gene. In such an event, direct activation by p53 would require the presence of a short-lived co-activator protein and possibly be mediated through a DNA response element distinct from the p53 20 bp consensus binding-site [El-Deity, W. S. et al, Nature Genetics 1, 45–49 (1992)], as dictated by the putative co-activator. Cloning and characterization of the promoter should address this issue.

This study shows that p53 activates multiple target genes in Saos-2 cells. Whether the proteins encoded by the low-abundance class transcripts could be particularly potent growth inhibitors remains to be established. Saos-2-D4H cells actually do only moderately slow down in their growth rate upon induction of p53 at the permissive temperature (data not shown). The reason for this is unclear, but may involve the fact that these cells are also negative for endogenous RB expression. Thus, we extended our studies to a different cell type, a colorectal carcinoma cell line (EB cells) that upon cadmium-mediated induction of an integrated wt p53 gene, has been demonstrated to undergo apoptosis, both in vitro and in vivo as an established tumor [Shaw, P. et al, Proc. Natl. Acad. Sci. U.S.A. 89, 4495–4499 (1992)]. Our results show that the WAF1/CIP1/p21 RNA, and the transcripts encoding A28 and A26, are efficiently and specifically increased upon induction of wt p53. Induction was more pronounced for the A28-encoding RNA than for the WAF1/CIP1/p21 and A26-encoding RNAs. As induction of these transcripts occurs in a cell type undergoing p53-mediated apoptosis, it is possible that the encoded proteins may represent downstream effectors in the p53 signaling pathway involved in programmed cell death. Further analysis will be required to study this possibility.

In summary, we show that p53 may activate multiple signaling pathways through its ability to act as a transcriptional activator. Thus, the activation of mutiple effectors may be involved in mediating the functions of p53 as a tumor suppressor.

EXAMPLE II

Cloning and Analysis of Full Length cDNA Corresponding to A28 cDNA Fragment

A specific cDNA fragment, called A28 (see Example I), was demonstrated to recognize a p53 regulated transcript of approximately 2.5 kb. This probe was used to clone the corresponding full-length cDNA. The cDNA was sequenced and the predicted encoded protein identified.

A. Cloning of cDNA corresponding to the A28 cDNA fragment.

Northern blots containing poly-adenylated RNA from multiple human tissues (obtained from Clonetech, Palo Alto, Calif.) were probed with the A28 cDNA fragment (Northern blot analysis as described in Example I hereinabove). This analysis revealed that all tissues analyzed expressed varying amounts of an A28 corresponding transcript, approximately 2.5 kb in size, with the possible exception of periphereal blood leukocytes (FIG. 8). Strong expression was detected in brain.

A human brain cDNA library was purchased from Stratagene (La Jolla, Calif.). $1 \times 10^6$ phage were screened using a $^{32}$P labeled A28 probe ($1 \times 10^6$ cpm/ml) under conditions described by the library producer (Stratagene) with the following modifications. The hybridization solution was: 50% formamide, 5×SSPE (1XSSPE=0.15M NaCL, 0.01M NaH$_2$PO$_4$, 1.25 mM EDTA, pH7.4), 5× Denhardt's solution [Eds Ausubel et al, In Current Protocols In Molecular Biology, John Wiley and Sons Publishers, New York, N.Y. (1988)], and 50 ug/ml denatured herring sperm DNA. Hybridization was carried out by incubation at 42° overnight. Blots were washed 3 times for 15 minutes with an excess of wash buffer (2×SSPE, 1% SDS), at room temperature, followed by a 15 minute wash in 0.2×SSPE, 0.1% SDS at 65° C.

Hybridizing plaques were purified through a secondary round of screening. Three clones containing cDNAs ranging from 1.5 to 2.0 kb were analyzed further. The longest clone, A28-15B, was rescued as a pBluescript plasmid (described in methods provided by Stratagene). A28-15B was sequenced using vector specific primers (T3, T7, KS, SK, see Bluescript, Stratagene) and gene specific primers (FIG. 9). A28-15B was 1969 nts (415-2383 of the sequence shown in FIG. 6 [SEQ. ID NO: 1]). It appeared not to be full-length based on size discepancy with Northern blots and the fact that the sequence began in the middle of the putative open reading frame.

B. 5' RACE of A28 sequences.

In order to obtain the missing 5' sequence a technique using a combination of reverse transcribed RNA, single strand anchor primer ligation and PCR with nested primers (collectively termed 5' RACE), was performed using a kit obtained from Clonetech. The protocol was followed according to the manufacturers directions and briefly described below. Poly-adenylated RNA from EB1 cells (described in Example I hereinabove), was reverse transcribed using LB57 primer (FIG. 9). The anchor was ligated to the first strand cDNA. Sequential PCR was then performed with the anchor primer and LB 57, and then with the anchor primer and LB 44 (FIG. 9). An approximately 1000 base pair product was obtained and sequenced with anchor and LB 50 as above. The sequence overlapping A28-15B was identical, but also extended approximately 415 bases further 5' (FIGS. 6 and 9). This product was sequenced and information obtained predicted that it contained the translational start site and missing protein coding region (see below). In addition its size, when the 5' RACE product was aligned with the A28-15B sequence, suggested that it was close to full-length C. Construction of an A28 full-length clone.

The A28-15B partial cDNA clone contains a unique Bgl II restriction site 16 nucleotides from its 5' end. Thus, A28-15B was digested with BglII and SmaI, present only in the polylinker (all restriction enzymes were purchased from Boehringer Mannheim, Indianapolis, Ind., and used according to the manufacturer's specifications). The PCR 5' cDNA fragment was digested with Bgl II and cloned into the digested A28-15B yielding pBS-A28. Faithful insertion was confirmed by sequencing. The sequence of the constructed full-length clone is given in FIG. 6 [SEQ ID NO: 1]. All sequence generated by PCR were also confirmed by sequencing the corresponding genomic sequence derived from a cosmid clone, identified with the original A28 cDNA fragment. Plasmid pBS-A28.7 in an *Escherichia coli* host cell (strain D45α) was deposited with the American Type Culture Collection, Rockville, Md., on Jun. 29, 1994, under the Budapest Treaty and assigned ATCC accession No. 69649. Upon granting of a United States patent, all restrictions on the availability to the public of the deposited cell line will be irrevocably removed. The deposit will be replaced if viable samples cannot be dispensed by the depository.

D. Analysis of full-length A28 cDNA.

The protein predicted to be encoded by the A28 cDNA is 202 amino acids (FIG. 7 [SEQ. ID No.2]), and hereby known as PIGI-1 protein. The predicted protein begins with the initiating methionine (ATG) at nucleotide 93, and continues to the stop codon (TGA) at nucleotide 740. The ATG is preceded by sequences associated with translation start sites [Kosak, M., Nucl. Acids Res. 20, 8125–8132 (1987)]. The predicted protein has strong amino acid homology with two predicted proteins of similar size, but of unknown function, present in GenBank (HUMGOS8PPC, 44.3% identity over 185 amino acids, and Hslr20rna, 48.3% over 147 amino acids).

E. Expression of PIGI-1 sense and antisense in vitro and in vivo.

Full-length PIGI-1 cDNA was cloned into a eukaryotic/prokaryotic expression vector, pCDNA3 (Invitrogen, San Diego, Calif.). This was accomplished by subcloning the EcoRI flanked cDNAs from pBS-A28 (the 3' EcoRI sites was the original cloning site for the cDNA library and the 5' EcoRI site was generated by the anchor primer in 5' RACE) into pCDNA3 (Invitrogen, San Diego, Calif.). Briefly, the 2.4 EcoRI fragment was resolved from the vector on a 0.8% agarose gel, and the excised DNA band was purified using Gene Clean (Bio 101, La Jolla, Calif.). The pCDNA3 vector was prepared by digestion with EcoRI, followed by treatment with calf intestinal phosphatase (Boehringer Mannheim, Indianapolis, Ind.) and Gene Clean purification. The insert was mixed with phosphatase-treated vector in a 5:1 molar ratio and ligated with T4 DNA ligase (Boehringer Mannhelm) for 1 hour at 14° C. 10 ng of ligated DNA was used to transform competent *E. coli* strain DH5α, according to the manufacturer's directions (GibcoBRL Life Technologies, Grand Island, N.Y.). Recombinants were selected on LB ampicillin plates [Maniatis et al., Molecular Cloning: A Laboratory Manual, Cold Spring Harbor Laboratory, N.Y. (1982)]. Recombinants were analyzed by preparing plasmid produced from liquid cultures using Qiagen plasmid purification columns (Qiagen, Chatsworth, Calif.) and digesting with either ApaI or BamHI to diagnostically determine orientation (both enzymes cut the vector and the insert each one time), yielding pCDNA3-PIGI-1 and pCDNA3-PIGI-1AS (anti-sense).

These plasmids were used as a template to produce RNA, and subsequently protein, using a coupled in vitro transcription/translation system (TNT, Promega, Madison, Wis.), according to the manufacturer's directions. $^{35}$S methionine (Amershan, Arlington Heights, Ill.) was used to label the in vitro translation products (according to the manufacturer, Promega), which were fractionated on an SDS polyacrylamide gel (Novex, San Diego, Calif.) and visualized after exposure to phosphorimaging plates (Fuji, Stamford, Conn.). An approximately 23 kD/product is detected by the extract programmed with pCDNA-PIGI-1 (FIG. 10). This is close to the predicted size of 22.7 kD. The extract programmed with antisense showed no specific protein product. No translation product is observed with the PIGI-1 antisense expression vector (pCDNA3-PIGI-1AS).

An approximately 8 KD product was detected in translation reactions programmed with the A28-15B truncation. A28-15B begins at position nt 416 of full-length PIGI-1, and an ATG at nucleotide 493 is noted that appears to conform to Kozak's initiation rules; however, this would only encode a 5 amino acid peptide before reaching a stop codon, and thus is not responsible for the observed product. The next potential initiating methionine (ATG) is at position 517, conforms to Kozak's rules, is inflame with the predicted PIGI-1 protein, and is predicted to encode the 61 C-terminal amino acids. The size of this product would be 7.4 kD and is consistent with the size of the observed in vitro translation product produced with the pCDNA3-A2815B programmed lysates.

F. PIGI-1 Protein Suppresses Tumor Cell Growth.

PIGI-1 protein was shown to be directly induced by p53. Since p53 is a known tumor suppressor shown to regulate at least two genes, WAF1/p21 and Gadd45, having growth inhibitory properties of their own, we examined the effects of PIGI-1 on growth of human tumor cells. Eukaryotic expression vectors pCDNA3-PIGI-1, pCDNA3-PIGI-1AS, wild-type p53, or the vector pDCNA3 were transfected using cationic lipid (Lipofectamine, Gibco, Grand Island, N.Y.), into EB colon carcinoma cells (obtained from Dr.

Phillip H. Shaw, Institut de Pathologie, Lausanne, Switzerland), HeLa cervical carcinoma or Saos2 osteosarcoma cell lines (both obtained from ATCC, Rockville, Md.). Cells were grown in the presence of G418 and colonies were scored after approximately 2 weeks of selection. Results with A28-15B suggest that the 61 carboxy terminal amino acids of PIGI-1 protein are capable of mediating tumor cell growth suppression as well (data not shown).

Consistent with its tumor suppressor function, we observed a strong reduction in the growth of all cell lines transfected with p53, ranging from 88–100% reduction in colony formation as compared to the control plasmid, pCDNA3 (Table 1). Expression of the PIGI-1 RNA also leads to a reduction in growth of human tumor cells, Saos-2 and EB (97 and 82%, respectively) as well as from other mammalian species; COS7 monkey cells and NIH 3T3 mouse cells (61 and 90% growth inhibition by PIGI-1 respectively). Expression of antisense PIGI-1 (PIGI-1-AS) had no appreciable effect on cell growth of COS7 cells (110% of vector) but, in the human lines Saos 2 and EB, appeared to actually provide a slight growth advantage (200% and 179% respectively). This may indicate that antisense PIGI-1 is inhibiting endogenous PIGI-1 mRNA (stability or expression), thus, further indicating that endogenous PIGI-1 is involved in cellular growth functions.

Consistent with p53's role in the DNA damage response, we have found that, like WAF1 [EI-Deiry et al., Cancer Res. 54, 169–1174 (1994)], PIGI-1 is induced by DNA damaging agents such as adriamycin or ultraviolet irradiation (data not shown), and that this induction correlates with the p53 status of the cell. Therefore, activation of PIGI-1 could represent an important step in the cellular growth inhibitory and/or apoptotic response to DNA damage. Furthermore, novel chemotherapeutics targeting PIGI-1 may replace conventional chemotherapeutic drugs that directly or indirectly target p53. These novel chemotherapeutics should be effective even in tumor cells that lack expression of normal p53.

TABLE 1

Effect of PIGI-1 gene expression on growth of culture cells

| Cell Line | PIGI-1 | pCDNA3 | PIGI-1-AS | p53 |
|---|---|---|---|---|
| Saos 2 | 3 (0–15) | 100 | 200 | 10 (2–17) |
| EB | 18 (0–33) | 100 | 179 | 12 (7–19) |
| COS7 | 29 (19–38) | 100 | ND | 0 |
| NIH 3T3 | 10 (4–19) | 100 | 110 | 4 (2–7) |

Tissue culture cells (3 × 10$^5$ per well) were transfected with the indicated plasmid construct (2ug) and were selected in G418 containing media (500 U/ml, except EB cells 800 U/ml) for approximately 2 weeks. Cells were washed and stained with formalin-crystal violet. Numbers represent the mean fraction of surviving colonies as compared to cells transfected with the control plasmid pCDNA3 (transfections were repeated 3 times in duplicate wells using different DNA preparations, except for antisense, which represents duplicate transfections). The range of the fraction of surviving colonies is indicated in brackets. ND indicates not done.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 2383 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
GGGGCTACCG CGCCTTTGCT TCCTGGCGCA CGCGGAGCCT CCTGGAGCCT GCCACCATCC      60

TGCCTACTAC GTGCTGCCCT GCGCCCGCAG CCATGTGCCG CACCCTGGCC GCCTTCCCCA     120

CCACCTGCCT GGAGAGAGCC AAAGAGTTCA AGACACGTCT GGGGATCTTT CTTCACAAAT     180

CAGAGCTGGG CTGCGATACT GGGAGTACTG GCAAGTCCGA GTGGGGCAGT AAACACAGCA     240

AAGAGAATAG AAACTTCTCA GAAGATGTGC TGGGGTGGAG AGAGTCGTTC GACCTGCTGC     300

TGAGCAGTAA AAATGGAGTG GCTGCCTTCC ACGCTTTCCT GAAGACAGAG TTCAGTGAGG     360

AGAACCTGGA GTTCTGGCTG GCCTGTGAGG AGTTCAAGAA GATCCGATCA GCTACCAAGC     420

TGGCCTCCAG GGCACACCAG ATCTTTGAGG AGTTCATTTG CAGTGAGGCC CCTAAAGAGG     480

TCAACATTGA CCATGAGACC CGCGAGCTGA CGAGGATGAA CCTGCAGACT GCCACAGCCA     540

CATGCTTTGA TGCGGCTCAG GGGAAGACAC GTACCCTGAT GGAGAAGGAC TCCTACCCAC     600

GCTTCCTGAA GTCGCCTGCT TACCGGGACC TGGCTGCCCA AGCCTCAGCC GCCTCTGCCA     660
```

| | | | | | |
|---|---|---|---|---|---|
| CTCTGTCCAG | CTGCAGCCTG | GACGAGCCCT | CACACACCTG | AGTCTCCACG | GCAGTGAGGA | 720
| AGCCAGCCGG | GAAGAGAGGT | TGAGTCACCC | ATCCCCGAGG | TGGCTGCCCC | TGTGTGGGAG | 780
| GCAGGTTCTG | CAAAGCAAGT | GCAAGAGGAC | AAAAAAAAAA | AAAAAAAAAA | AAAAAATGCG | 840
| CTCCAGCAGC | CTGTTTGGGA | AGCAGCAGTC | TCTCCTTCAG | ATACTGTGGG | ACTCATGCTG | 900
| GAGAGGAGCC | GCCCACTTCC | AGGACCTGTG | AATAAGGGCT | AATGATGAGG | GTTGGTGGGG | 960
| CTCTCTGTGG | GGCAAAAAGG | TGGTATGGGG | GTTAGCACTG | GCTCTCGTTC | TCACCGGAGA | 1020
| AGGAAGTGTT | CTAGTGTGGT | TTAGGAAACA | TGTGGATAAA | GGGAACCATG | AAAATGAGAG | 1080
| GAGGAAAGAC | ATCCAGATCA | GCTGTTTTGC | CTGTTGCTCA | GTTGACTCTG | ATTGCATCCT | 1140
| GTTTTCCTAA | TTCCAGACT | GTTCTGGGCA | CGGAAGGGAC | CCTGGATGTG | GAGTCTTCCC | 1200
| CTTTGGCCCT | CCTCACTGGC | CTCTGGGCTA | GCCAGAGTC | CCTTAGCTTG | TACCTCGTAA | 1260
| CACTCCTGTG | TGTCTGTCCA | GCCTTGCAGT | CATGTCAAGG | CCAGCAAGCT | GATGTGACTC | 1320
| TTGCCCCATG | CGAGATATTT | ATACCTCAAA | CACTGGCCTG | TGAGCCCTTT | CCAAGTCAGT | 1380
| GGAGAGCCCT | GAAAGGAGGC | TCACTTGAAT | CCAGCTCAGT | GCTCTGGGTG | GCCCCCTGCA | 1440
| GGTGGCCCCT | GACCCTGCGT | TGCAGCAGGG | TCCACCTGTG | AGCAGGCCCG | CCCTGGGGCC | 1500
| TCTTCCTGGA | TGTGCCCTCT | CTGAGTTCTG | TGCTGTCTCT | TGGAGGCAGG | GCCCAGGAGA | 1560
| ACAAAGTGTG | GAGGCCTCGG | GGAGTGGCTT | TTCCAGCTCT | CATGCCCCGC | AGTGTGGAAC | 1620
| AAGGCAGAAA | AGGATCCTAG | GAAATAAGTC | TCTTGGCGGT | CCCTGAGAGT | CCTGCTGAAA | 1680
| TCCAGCCAGT | GTTTTTGTG | GTATGAGAAC | AGGCAAAAAG | AGATGCCCCG | AGATAGAAGG | 1740
| GGAGCCTTGT | GTTTCTTTCC | TGCAGACGTG | AGATGAACAC | TGGAGTGGGC | AGAGGTGGCC | 1800
| CAGGACCATG | GCACCCTTAG | AGTGCAGAAG | CTGGGGGGAG | AGGCTGCTTC | GAAGGGCAGG | 1860
| ACTGGGGATA | CCTGCCTGTC | ACCTCAGGGC | ATCACTGAAC | AAACATTTCC | TGATGGGAAC | 1920
| TCCTGCGGCA | GAGCCCAGGC | TGGGGAAGTG | AACTACCCAG | GGCAGCCCCT | TTGTGGCCCA | 1980
| GGATAATCAA | CACTGTTCTC | TCTGTACCAT | GAGCTCCTCC | AGGAGATTAT | TTAAGTGTAT | 2040
| TGTATCATTG | GTTTCTGTG | ATTGTCATAA | CATTGTTTTT | GTTATTGTTG | GTGCTGTTGT | 2100
| TATTTATTAT | TGTAATTTCA | GTTTGCCTCT | ACTGGAGAAT | CTCAGCAGGG | GTTTCAGCCT | 2160
| GACTGTCTCC | CTTTCTCTAC | CAGACTCTAC | CTCTGAATGT | GCTGGGAACC | TCTTGGAGCC | 2220
| TGTCAGGAAC | TCCTCACTGT | TTAAATATTT | ATTTATTGTG | ACAAATGGAG | CTGGTTTCCT | 2280
| AGATATGAAT | GATGTTTGCA | ATCCCCATTT | TCCTGTTTCA | GCATGTTATA | TTCTTATAAA | 2340
| ATAAAAGCAA | AAGTCAAATA | TGAAAAAAAA | AAAAAAAAAA | AAA | | 2383

( 2 ) INFORMATION FOR SEQ ID NO:2:

( i ) SEQUENCE CHARACTERISTICS:
        ( A ) LENGTH: 202 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Cys  Arg  Thr  Leu  Ala  Ala  Phe  Pro  Thr  Thr  Cys  Leu  Glu  Arg  Ala
  1              5                       10                      15

Lys  Glu  Phe  Lys  Thr  Arg  Leu  Gly  Ile  Phe  Leu  His  Lys  Ser  Glu  Leu
            20                      25                      30

Gly  Cys  Asp  Thr  Gly  Ser  Thr  Gly  Lys  Ser  Glu  Trp  Gly  Ser  Lys  His
       35                      40                      45

Ser  Lys  Glu  Asn  Arg  Asn  Phe  Ser  Glu  Asp  Val  Leu  Gly  Trp  Arg  Glu
```

|     | 50  |     |     |     |     | 55  |     |     |     |     | 60  |     |     |     |     |
|-----|-----|-----|-----|-----|-----|-----|-----|-----|-----|-----|-----|-----|-----|-----|-----|
| Ser 65 | Phe | Asp | Leu | Leu | Leu 70 | Ser | Ser | Lys | Asn | Gly 75 | Val | Ala | Ala | Phe | His 80 |
| Ala | Phe | Leu | Lys | Thr 85 | Glu | Phe | Ser | Glu | Glu 90 | Asn | Leu | Glu | Phe | Trp 95 | Leu |
| Ala | Cys | Glu | Glu 100 | Phe | Lys | Lys | Ile | Arg 105 | Ser | Ala | Thr | Lys | Leu 110 | Ala | Ser |
| Arg | Ala | His 115 | Gln | Ile | Phe | Glu | Glu 120 | Phe | Ile | Cys | Ser | Glu 125 | Ala | Pro | Lys |
| Glu | Val 130 | Asn | Ile | Asp | His | Glu 135 | Thr | Arg | Glu | Leu | Thr 140 | Arg | Met | Asn | Leu |
| Gln 145 | Thr | Ala | Thr | Ala | Thr 150 | Cys | Phe | Asp | Ala | Ala 155 | Gln | Gly | Lys | Thr | Arg 160 |
| Thr | Leu | Met | Glu | Lys 165 | Asp | Ser | Tyr | Pro | Arg 170 | Phe | Leu | Lys | Ser | Pro 175 | Ala |
| Tyr | Arg | Asp | Leu 180 | Ala | Ala | Gln | Ala | Ser 185 | Ala | Ala | Ser | Ala | Thr 190 | Leu | Ser |
| Ser | Cys | Ser 195 | Leu | Asp | Glu | Pro | Ser 200 | His | Thr |     |     |     |     |     |     |

( 2 ) INFORMATION FOR SEQ ID NO:3:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

TCGAGCTTGC CTGGACTTGC CTGCCAGATC TGTCGACGGA GG      42

---

What is claimed is:

1. An isolated nucleic acid molecule comprising a nucleic acid sequence coding for p53 response protein PIGI-1 shown in FIG. 7 (SEQ. ID NO:2).

2. The nucleic acid molecule according to claim 1 which is a DNA molecule and wherein the nucleic acid sequence is a DNA sequence.

3. The DNA molecule according to claim 2 wherein the DNA sequence has the nucleotide sequence shown in FIG. 6.

4. A DNA molecule comprising a DNA sequence having all or part of the nucleotide sequence shown in FIG. 6 (SEQ. ID NO:1), wherein the DNA sequence having part of the nucleotide sequence shown in FIG. 6 (SEQ ID NO:1) is at least about 30 sequential nucleotides in length.

5. The DNA molecule according to claim 4 wherein the DNA sequence has the sequence of nucleotides 416–2383 shown in FIG. 6.

6. A DNA molecule having a DNA sequence which is complementary to the DNA sequence according to claims 2, 3, 4 or 5.

7. A nucleic acid molecule having a nucleic acid sequence which hybridizes to the nueleic acid sequence according to claim 1, wherein the hybridization wash buffer is 0.2×SSPE, 0.1% SDS and wherein the hybridization wash temperature is 65° C.

8. A DNA molecule having a DNA sequence which hybridizes to the DNA sequence according to claims 2, 3, 4 or 5, wherein the hybridization wash buffer is 0.2×SSPE, 0.170SSPE, 0.1% SDS and wherein the hybridization wash temperature is 65° C.

9. A DNA molecule having a DNA sequence which hybridizes to the DNA sequence according to claim 6, wherein the hybridization wash buffer is 0.2×SSPE, 0.1% SDS and wherein the hybridization wash temperature is 65° C.

10. An expression vector comprising a DNA sequence coding for p53 response protein PIGI-1 shown in FIG. 7 (SEQ ID NO:2).

11. The expression vector according to claim 10 wherein the DNA sequence coding for p53 response protein PIGI-1 has the nucleotide sequence as shown in FIG. 6.

12. A vector comprising a DNA sequence having all or part of the nucleotide sequence as shown in FIG. 6 (SEQ ID NO:1), wherein the DNA sequence having part of the nucleotide sequence shown in FIG. 6 (SEQ NO:1) is at least about 30 sequential nucleotides in length .

13. The vector according to claim 12 wherein the DNA sequence has the sequence of nucleotides 93–698 shown in FIG. 6.

14. The vector according to claim 13 which is an expression vector.

15. A prokaryotic or eukaryotic host cell comprising the expression vector according to claim 10.

16. A prokaryotic or eukaryotic host cell comprising the expression vector according to claim 11.

17. A prokaryotic or eukaryotic host cell comprising the vector according to claim 12.

18. A prokaryotic or eukaryotic host cell comprising the vector according to claim 13.

19. The prokaryotic or eukaryotic host cell according to claim 18 wherein the vector is an expression vector.

20. A method for producing a polypeptide molecule comprising p53 response protein PIGI-1, which comprises culturing a host cell according to claim 15 under conditions permitting expression of the polypeptide.

21. A method for producing a polypeptide molecule comprising p53 response protein PIGI-1, which comprises culturing a host cell according to claim 16 under conditions permitting expression of the polypeptide.

22. A method for producing a polypeptide molecule comprising p53 response protein PIGI-1, which comprises culturing a host cell according to claims 18 or 19 under conditions permitting expression of the polypeptide.

* * * * *